US009878028B2

(12) United States Patent
Chouvenc et al.

(10) Patent No.: US 9,878,028 B2
(45) Date of Patent: *Jan. 30, 2018

(54) PROCESS FOR STABILIZING AN ADJUVANT CONTAINING VACCINE COMPOSITION

(71) Applicant: SANOFI PASTEUR SA, Lyons (FR)

(72) Inventors: Pierre Chouvenc, Lyons (FR); Alain Francon, Brullioles (FR)

(73) Assignee: Sanofi Pasteur SA, Lyons (FR)

( * ) Notice: Subject to any disclaimer, the term of this patent is extended or adjusted under 35 U.S.C. 154(b) by 5 days.

This patent is subject to a terminal disclaimer.

(21) Appl. No.: 15/046,902

(22) Filed: Feb. 18, 2016

(65) Prior Publication Data
US 2016/0235831 A1 Aug. 18, 2016

Related U.S. Application Data

(62) Division of application No. 14/031,311, filed on Sep. 19, 2013, now Pat. No. 9,295,721, which is a division of application No. 12/397,140, filed on Mar. 3, 2009, now Pat. No. 8,551,527.

(60) Provisional application No. 61/044,090, filed on Apr. 11, 2008.

(30) Foreign Application Priority Data

Mar. 5, 2008 (EP) .................... 08290216

(51) Int. Cl.
A61K 9/14 (2006.01)
A61K 39/08 (2006.01)
A61K 39/385 (2006.01)
A61K 39/00 (2006.01)
A61K 9/19 (2006.01)
A61K 39/145 (2006.01)
C12N 7/00 (2006.01)
A61K 39/102 (2006.01)
A61K 39/05 (2006.01)
A61K 39/12 (2006.01)
A61K 39/02 (2006.01)
A61K 9/16 (2006.01)
C07K 14/285 (2006.01)
A61K 38/48 (2006.01)
A61K 47/26 (2006.01)

(52) U.S. Cl.
CPC ............ *A61K 39/08* (2013.01); *A61K 9/1623* (2013.01); *A61K 9/19* (2013.01); *A61K 39/0208* (2013.01); *A61K 39/05* (2013.01); *A61K 39/102* (2013.01); *A61K 39/12* (2013.01); *A61K 39/145* (2013.01); *C12N 7/00* (2013.01); *A61K 9/1617* (2013.01); *A61K 9/1694* (2013.01); *A61K 38/4893* (2013.01); *A61K 47/26* (2013.01); *A61K 2039/555* (2013.01); *A61K 2039/55505* (2013.01); *A61K 2039/6037* (2013.01); *A61K 2039/70* (2013.01); *C07K 14/285* (2013.01); *C12N 2760/16134* (2013.01); *C12N 2760/16151* (2013.01); *C12N 2760/16234* (2013.01); *C12N 2760/16334* (2013.01)

(58) Field of Classification Search
CPC .............. A61K 9/1694; A61K 38/4893; A61K 2039/6037; A61K 38/00
See application file for complete search history.

(56) References Cited

U.S. PATENT DOCUMENTS

| 3,162,019 A | 12/1964 | Porter et al. |
| 3,313,032 A | 4/1967 | Malecki |
| 3,431,655 A | 3/1969 | Grover et al. |
| 3,655,838 A | 4/1972 | Price et al. |
| 3,665,838 A | 4/1972 | Thompson et al. |
| 3,674,864 A | 7/1972 | Angelucci |
| 4,211,015 A | 7/1980 | Adams et al. |
| 4,500,512 A | 2/1985 | Barme |
| 4,848,094 A | 7/1989 | Davis et al. |
| 5,036,673 A | 8/1991 | Miller et al. |
| 5,307,640 A | 5/1994 | Fawzy et al. |
| 5,475,984 A | 12/1995 | Fermani et al. |
| 5,843,347 A | 12/1998 | Nguyen et al. |
| 5,897,852 A | 4/1999 | Wilderbeek et al. |
| 5,998,031 A | 12/1999 | Buhl et al. |
| 6,048,537 A | 4/2000 | Violay et al. |
| 6,210,683 B1 | 4/2001 | Burke et al. |
| 6,231,860 B1 | 5/2001 | Fanget et al. |

(Continued)

FOREIGN PATENT DOCUMENTS

| EP | 0 081 913 | 5/1985 |
| EP | 0 475 409 | 12/1991 |

(Continued)

OTHER PUBLICATIONS

Y. Guan et al.: "Emergence of multiple genotypes of H5N1 avian influenza viruses in Hong Kong SAR," PNAS, pp. 8950-8955, Jun. 25, 2002, vol. 99 No. 13.
Mikhail N. Matrosovich et al.: "H9N2Influenza A Viruses from Poultry in Asia Have Human Virus-like Receptor Specificity," Virology 281, pp. 156-162 (2001).
Robert G. Webster et al.: "Evolution and Ecology of Influenza A Viruses," Microbiological Reviews, Mar. 1992, pp. 152-179, vol. 56, No. 1.
A. C. Hulst et al.: "A New Technique for the Production of Immobilized Biocatalyst in Large Quantities," Biotechnol. Bioeng. 27, pp. 870-876 (1984).

(Continued)

Primary Examiner — Gary Nickol
Assistant Examiner — Lakia Jackson-Tongue
(74) Attorney, Agent, or Firm — McDonnell Boehnen Hulbert & Berghoff LLP

(57) ABSTRACT

The present invention relates to a process for stabilizing an adjuvant containing vaccine composition, an adjuvanted vaccine composition in dry form and in particular a process for stabilizing an influenza vaccine composition, particularly an adjuvanted influenza vaccine composition in dry form.

11 Claims, 19 Drawing Sheets

(56) References Cited

U.S. PATENT DOCUMENTS

Figure 1:
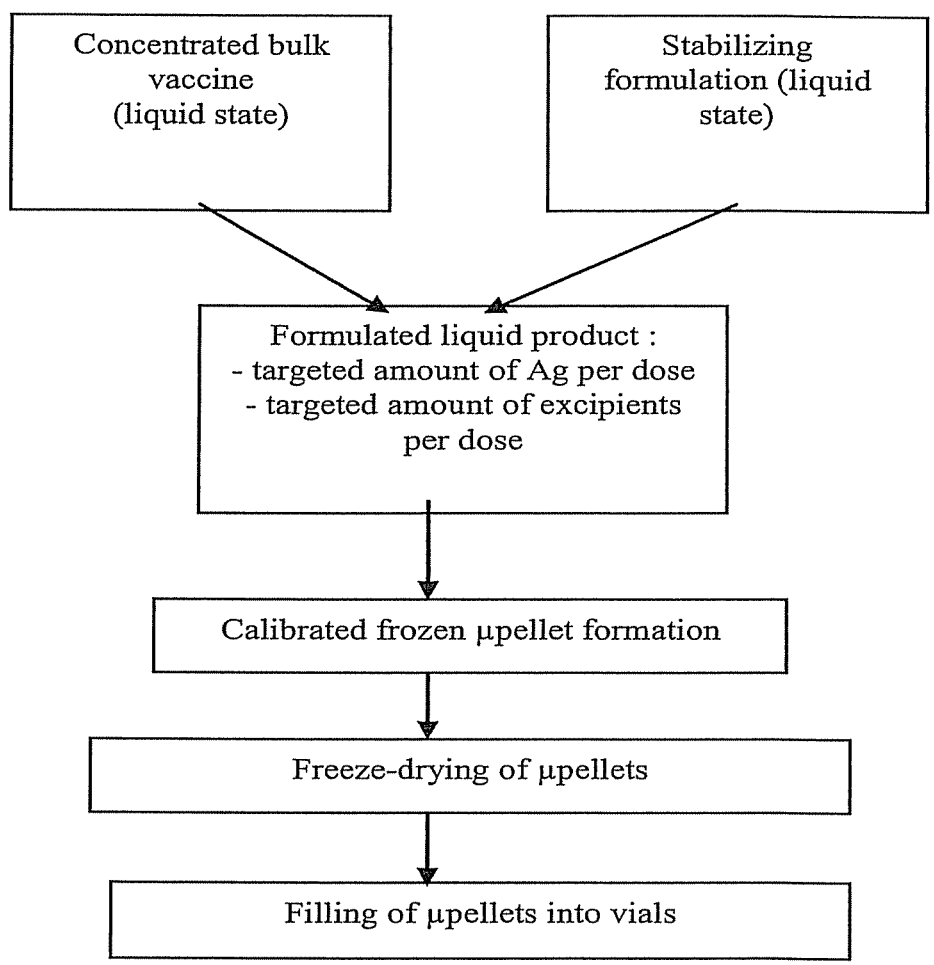

| | | | |
|---|---|---|---|
| 6,306,404 | B1 | 10/2001 | LaPosta et al. |
| 6,458,363 | B1 | 10/2002 | Schrier et al. |
| 6,589,522 | B1 | 7/2003 | Galler et al. |
| 6,696,281 | B1 | 2/2004 | Chambers et al. |
| 6,862,890 | B2 | 3/2005 | Williams et al. |
| 6,903,065 | B2 | 6/2005 | Nyssen et al. |
| 6,962,708 | B1 | 11/2005 | Chambers et al. |
| 7,238,349 | B1 | 7/2007 | D'Hondt et al. |
| 7,344,720 | B2 | 3/2008 | Haensler |
| 8,268,354 | B2 | 9/2012 | Truong-Le et al. |
| 8,551,527 | B2 * | 10/2013 | Chouvenc ............ A61K 9/1623 424/193.1 |
| 9,295,721 | B2 * | 3/2016 | Chouvenc ............ A61K 9/1623 |
| 2002/0120228 | A1 | 8/2002 | Maa et al. |
| 2004/0042972 | A1 | 3/2004 | Truong-Le et al. |
| 2004/0052818 | A1 | 3/2004 | Heinz et al. |
| 2004/0213745 | A1 | 10/2004 | Sullivan et al. |
| 2004/0213798 | A1 | 10/2004 | Maa et al. |
| 2005/0118275 | A1 | 6/2005 | O'Hagan |
| 2006/0002862 | A1 | 1/2006 | Truong-Le et al. |
| 2006/0165717 | A1 | 7/2006 | Dalencon et al. |
| 2007/0281067 | A1 | 12/2007 | Braithwaite |
| 2008/0014219 | A1 | 1/2008 | Barban et al. |
| 2008/0060213 | A1 | 3/2008 | Gehrmann et al. |
| 2008/0085288 | A1 | 4/2008 | Guy et al. |
| 2008/0131460 | A1 | 6/2008 | Guy et al. |

FOREIGN PATENT DOCUMENTS

| | | |
|---|---|---|
| EP | 0799613 | 10/1997 |
| EP | 2036572 | 3/2009 |
| EP | 1159968 | 12/2012 |
| GB | 1559920 | 1/1980 |
| WO | 93/06214 | 4/1993 |
| WO | WO 1994/25005 | 11/1994 |
| WO | 1996/05294 | 2/1996 |
| WO | 96/36317 | 11/1996 |
| WO | 96/40933 | 12/1996 |
| WO | 98/37911 | 9/1998 |
| WO | 00/57904 | 10/2000 |
| WO | 00/57908 | 10/2000 |
| WO | 00/57909 | 10/2000 |
| WO | 00/57910 | 10/2000 |
| WO | WO 01/28525 | 4/2001 |
| WO | 01/60847 | 8/2001 |
| WO | 01/93829 | 12/2001 |
| WO | 02/072835 | 9/2002 |
| WO | 02/095075 | 11/2002 |
| WO | 02/102828 | 12/2002 |
| WO | 03/101397 | 12/2002 |
| WO | WO 03/087339 | 10/2003 |
| WO | 03/102166 | 12/2003 |
| WO | 03/103571 | 12/2003 |
| WO | 04/045529 | 6/2004 |
| WO | WO 2004/073652 | 9/2004 |
| WO | WO 2004/073735 | 9/2004 |
| WO | 05/082020 | 9/2005 |
| WO | WO 2006/037070 | 4/2006 |
| WO | 06/134433 | 12/2006 |
| WO | 06/134443 | 12/2006 |
| WO | WO 2007/006939 | 1/2007 |
| WO | WO 2007/038926 | 4/2007 |
| WO | 07/056847 | 5/2007 |
| WO | WO 2007/073035 | 6/2007 |
| WO | WO 2008/009309 | 1/2008 |
| WO | 08/057550 | 5/2008 |
| WO | WO 2008/049633 | 5/2008 |
| WO | WO 2008/079464 | 7/2008 |

OTHER PUBLICATIONS

T. Gotoh et al.: "Mass-Production of Biocatalyst-entrapping Alginate Gel Particles by a Forced Oscillation Method," Chem. Eng. Commun. vol. 120, pp. 73-84 (1993).

Douglas B. Seifert et al.: "Production of Small, Monodispersed Alginate Beads for Cell Immobilization," Biotechnol. Prog. 1997, 13, pp. 562-568.

Lord Rayleigh, 1978, On the stability of jets. Proc. London Math Soc. 10, 4-13 for Newton fluids.

N. Al-Waili, "Topical honey application vs. acyclovir for the treatment of recurrent herpes simplex lesions," Med. Sci. Monit, 2004, 10(8), MT94-98.

W. Wang, "Lyophilization and development of solid protein pharmaceuticals," International Journal of Pharmaceutics, 2000, vol. 203, 1-60.

Amorij et al., "Development of stable Influenza vaccine powder formulations: challenges and possibilities," Pharmaceutical Research, vol. 25, 1256-1273 (2008).

Steven Schwendeman et al; Stabilization of tetanus and diphtheria toxoids against moisture-induced agreation; Proc. Natl. Acad. Sci. USA; vol. 92, pp. 11234-11238 (1995).

P. Matejtschuk et al; "Optimization of the formulation for a candidate lyophilised tetanus toxoid reference preparation," Biologicals 37 (2009) 1-7.

D. Sindayihebura et al; "Experimental study of thin liquid fiml ultrasonic atomization," ExHFT'97, Bruxelles (1997).

H. Brandenberger et al; "A new multinozzle encapsulation/immobilisation system to produce uniform beads of alginate," J. biotechnology, 63, 73-80 (1998).

M.S. Williams; "Single-radial-immunodiffusion as an in vitro potency assay for human inactivated viral vaccines," Veterinary Microbiology, 37 (1993) 253-262.

"Spray Engineering Handbook" at the URL: http://www.pnr-france.fr/site-web/IMG/pdf/ENGINEERING_HANDBOOD_CTG_SH07_BR.pdf. A search at Internet Archive retrieves a first archive dated Jul. 21, 2014.

"Nisco" at the URL: http://www.nisco.ch/working_principle_electromagnetic.htm. A search at Internet Archive (http://archive.org/web/web.php) retrieves a first archive dated Jan. 9, 2012.

Siddheshwar et al., "Powderject Device: A Needle Free Tool for Transdermal Drug Delivery," Mar. 28, 2013, Dermal PowderJect Device Archives—Pharma Research Library, http://www.pharmaresearchlibrary.com/tag/dermal-powderject-device/.

Cox et al., "Adjuvants—a classification and review of their modes of action", Vaccine, 1997, 15(3), 248-256.

Guy, B., "The perfect mix: recent progress in adjuvant research", Nature Reviews Microbiology, 2007, 5(7), 505-517.

Adebayo et al., Biologicals, 26:309-316, 1998.

Barme et al., J. Biol. Stand., 12:435-442, 1984.

Galler et al., Vaccine, 16:1024-1028, 1998.

Lai et al., Adv. Virus Res., 61:469-509, 2003.

Rayleigh, "On the Instability of Jets," Proc. Lond. Math. Soc., 10:4-12, 1878.

Rice et al., Science, 229:726-733, 1985.

Sood et al., Vaccine, 11:1124-1128, 1993.

Theiler et al., J. Exp. Med., 65:787-800, 1937.

Toriniwa et al., Vaccine, 26:3680-3689, 2008.

International Search Report of International Application No. PCT/EP2009/004980, dated Oct. 2 and Oct. 13, 2009.

Written Opinion from International Application No. PCT/EP2009/004980, dated Oct. 2 and Oct. 13, 2009.

http://www.sonozap.com/Atomizer_Nozzles.html; publication date of Nov. 11, 2006.

https://web.archive.org/web/20061111101013/http://www.sonozap.com/Atomizer_Nozzles.html; publication date of Nov. 11, 2006.

http://www.pathtech.com.au/files/0K1G0N7A9A953H2G5U4A901T8H7Y/PrillingCoextrusionTechnology.pdf; publication date of Jun. 20, 2005.

http://www.bd.com/press/pdfs/flu/bd_accuspray.pdf, publication date of Mar. 12, 2006.

* cited by examiner

General formulation and drying procedure

Flow chart of the general formulating, freezing and drying procedure comprising an adjuvant

Figure 4:

Production of antigen micropellets

```
┌─────────────────────┐         ┌─────────────────────┐
│ Concentrated bulk   │         │    Stabilizing      │
│     vaccine         │         │ formulation (liquid │
│  (liquid state)     │         │       state)        │
└──────────┬──────────┘         └──────────┬──────────┘
           └────────────┐   ┌──────────────┘
                        ▼   ▼
          ┌─────────────────────────────────┐
          │   Formulated liquid product :   │
          │  - targeted amount of Ag per dose│
          │  - targeted amount of excipients│
          │            per dose             │
          └────────────────┬────────────────┘
                           ▼
          ┌─────────────────────────────────┐
          │ Calibrated frozen μpellet formation│
          └────────────────┬────────────────┘
                           ▼
          ┌─────────────────────────────────┐
          │     Freeze-drying of μpellets   │
          └────────────────┬────────────────┘
                           ▼
          ┌─────────────────────────────────┐
          │   Filling of μpellets into vials│
          └─────────────────────────────────┘
```

Production of adjuvant micropellets

Combination of the different micropellets to the complete dry vaccine

Flow-chart of the formulation and drying procedure as described in Example 1

Narrow size distribution of the micropellets obtained in Example 1

Figure 10

Flow-chart of the formulation and drying procedure as described in Example 2

```
┌─────────────────────┐         ┌─────────────────────┐
│  H5N1 flu Vaccine,  │         │     Stabilizing     │
│                     │         │     formulation     │
│ Aluminum hydroxide  │         │ (carbohydrate solution│
│     adjuvanted,     │         │         SG1)        │
└──────────┬──────────┘         └──────────┬──────────┘
           │                               │
           └───────────────┬───────────────┘
                           ▼
              ┌─────────────────────────┐
              │  Formulated liquid      │
              │      product :          │
              │  - 1 vaccinale dose/mL  │
              │  - 100g/L sucrose       │
              └────────────┬────────────┘
                           ▼
              ┌─────────────────────────┐
              │ Calibrated frozen μpellet formation │
              └────────────┬────────────┘
                           ▼
              ┌─────────────────────────┐
              │ Freeze-drying of μpellets │
              └────────────┬────────────┘
                           ▼
              ┌─────────────────────────┐
              │ Filling of μpellets into vials │
              └─────────────────────────┘
```

Aluminum oxyhydroxide gel particle size before and after micropellet processing. SG1 stabilizer.

Aluminum oxyhydroxide gel particle size after thermostability incubation 7 days at 37°C, 45°C and 55°C dissolution with WFI.

Figure 13

```
┌─────────────────┐        ┌─────────────────┐
│    H5N1 Flu     │        │   Stabilizing   │
│  vaccine non-   │        │   formulation   │
│    adjuvanted   │        │  (carbohydrate  │
│                 │        │  solution SG-1) │
└────────┬────────┘        └────────┬────────┘
         │                          │
         └────────────┬─────────────┘
                     ▼
         ┌───────────────────────┐
         │   Formulated          │
         │   liquid product :    │
         │   -1dose/0.5ml        │
         │   -154g/L of          │
         │    sucrose            │
         └───────────┬───────────┘
                     ▼
    ┌──────────────────────────────────┐
    │ Calibrated frozen micropellets formation │
    └──────────────┬───────────────────┘
                   ▼
    ┌──────────────────────────────────┐
    │   Freeze-drying of micropellets  │
    └──────────────┬───────────────────┘
                   ▼
    ┌──────────────────────────────────┐
    │   Filling of micropellets into vials │
    └──────────────────────────────────┘
```

Figure 16

```
┌─────────────────┐      ┌─────────────────┐
│   H5N1 Flu      │      │   Stabilizing   │
│  vaccine non-   │      │   formulation   │
│   adjuvanted    │      │  (carbohydrate  │
│                 │      │   solution SG8) │
└────────┬────────┘      └────────┬────────┘
         │                        │
         └───────────┬────────────┘
                    ▼
         ┌────────────────────┐
         │    Formulated      │
         │  liquid product :  │
         │   -1dose/0.5ml     │
         │    -20g/L of       │
         │     sucrose        │
         └─────────┬──────────┘
                   ▼
  ┌──────────────────────────────────────┐
  │ Calibrated frozen micropellets formation │
  └──────────────────┬───────────────────┘
                     ▼
       ┌──────────────────────────────┐
       │ Freeze-drying of micropellets │
       └──────────────┬───────────────┘
                      ▼
       ┌──────────────────────────────┐
       │ Filling of micropellets into vials │
       └──────────────────────────────┘
```

PROCESS FOR STABILIZING AN ADJUVANT CONTAINING VACCINE COMPOSITION

This application is a divisional of U.S. patent application Ser. No. 14/031,311 filed Sep. 19, 2013, which is a divisional of U.S. patent application Ser. No. 12/397,140 filed Mar. 3, 2009, now U.S. Pat. No. 8,551,527, which claims the benefit of priority of U.S. Provisional Application No. 61/044,090 filed Apr. 11, 2008 and European Application No. 08290216.4 filed Mar. 5, 2008, the entire contents of each of which are hereby incorporated by reference into the present specification.

BACKGROUND OF THE INVENTION

Field of the Invention

The present invention relates to a process for stabilizing an adjuvant containing vaccine composition, an adjuvanted vaccine composition in dry form and in particular a process for stabilizing an influenza vaccine composition, particularly an adjuvanted influenza vaccine composition in dry form.

Description of Related Art

U.S. Pat. No. 3,655,838 discloses a method of pelletizing analytical or immunological reagents by freezing droplets of solutions in a freezing medium, such as liquid nitrogen, and subsequent freeze drying in order to obtain freeze-dried, reagent containing micro-particles, spherical beads or lyospheres. EP 0 081 913 B1 describes a method for producing spherical frozen particles by freezing droplets in an inert liquid freezing medium with a higher density than the droplets and removing the frozen particles from the surface of the liquid freezing medium. WO 94/25005 discloses the stabilization of gonadotropin in lyospheres, a method for making such lyospheres and pharmaceutical preparations comprising the same. EP 0 799 613 (U.S. Pat. No. 5,897,852) discloses a vaccine pack that comprises a vaccine container containing one ore more freeze-dried bodies containing the vaccine components, at least one of which being a lyosphere or micro-particle having a diameter of at least 0.2 mm. WO 2006/008006 (US 2008/0060213) discloses a process for producing containers filled with a freeze-dried product wherein droplets of the product are frozen to form pellets, the pellets are freeze dried, assayed and loaded into the containers. Other techniques for obtaining frozen particles or pellets are known for application in the food industry (e.g. U.S. Pat. No. 5,036,673 or US 2007/0281067 A1).

The freeze drying technology allows improving the stability of a lot of products which can be a vaccine with or without adjuvant. For example EP 0 475 409 discloses a method for preserving a buffer and optionally a cryoprotectant containing suspension of microscopic biological material by nebulizing the suspension to microdroplets, freezing the droplets on a rotating cryogenic surface and drying the microdroplets. Preferably the droplets have a diameter of about less than 200 µm.

The freeze-drying of flu antigens has been studied in the literature and a detailed review is available (Amorij et al. 2008: Development of stable Influenza vaccine powder formulations: challenges and possibilities. Pharmaceutical Research, Vol 25, 1256-1273). U.S. Pat. No. 3,674,864 discloses a process for stabilizing influenza virus vaccines essentially by suspending the virus in an aqueous sucrose containing solution and freeze-drying the suspension. Also the stabilization of *tetanus* and *diphtheria* toxoids has been discussed in the literature (see e.g. S. P. Schwendeman et al., Proc. Natl. Acad. Sci. USA Vol. 92, pp. 11234-11238, 1995).

Very recently, optimized formulations for lyophilizing *tetanus* toxoid have been proposed (P. Matejtschuk et al. Biologicals 37 (2009) 1-7).

Usually the freeze drying is a final step in the pharmaceutical industry, coming after the filling step in vials, syringes or larger containers. In this case the dried product has to be rehydrated (synonyms in this document: reconstituted or dissolved) before its use.

Freeze drying in the form of micropellets allows the same stabilization of the dried vaccine product as for mere freeze-drying alone or it improves stability for storage. Furthermore, the micropellets technology offers several advantages in comparison to the current freeze drying, since it allows e.g.

blending of the dried products before filling (or by sequential filling)

titer adjustment before filling (which can be used in case of stock piling)

minimizing the interaction between products (there is only product interaction after rehydration), and improvement of the stability in some cases.

For these reasons the advantage of the micropellets technology allows several approaches for the drying of adjuvanted vaccine:

The drying of the antigens together with the adjuvant (being in the same phase): to stabilize the two (antigens and adjuvant) and to stabilize the interaction between them by trapping them in a glassy matrix in which all molecular motions and chemical reactions are greatly hindered. This solid state allows to maintain throughout storage (even at higher temperature) potency of the antigen, physical and immunological properties of the adjuvant and nature and force of the interaction between the two.

The drying of the antigens and the separate drying of the adjuvant (antigen and adjuvant being in different phases), followed by blending of the two before the filling or by a sequential filling. In some cases, stability of the adjuvant alone can be a problem (chemical stability of emulsions, physical stability of aluminum gels, liposomes and others . . . ) at the liquid state for long-term storage at +5° C. or higher or at lower temperatures. The micropellet technology allows improving stability of the adjuvanted vaccine by generating separate micropellets of antigen and adjuvant. The stabilizing formulation can be optimized independently for each antigens and the adjuvant. The micropellets of antigens and adjuvants can be then subsequently filled into the vials or blended before filling into the vials. The separated solid state allows to avoid throughout storage (even at higher temperature) interactions between antigen and adjuvant, to maintain the potency of the antigen and physical and the immunological properties of the adjuvant. In such a configuration, the content of the vial can be more stable than any other configurations with either one of the antigens or the adjuvants in the liquid state or when antigens and adjuvant are dried within the same pellets. Interactions between antigens and adjuvants are this way standardized as they occur only after rehydration of the dry combination with a selected diluent which may comprise water for injection, buffers and stabilizing excipients. Interactions are therefore to be controlled only during the short period of time between rehydration and injection of the vaccine.

It is therefore possible to improve the overall stability of the two products can be improved (optimization of the formulation for each product and not a compromise for the two together) and the vaccine itself, adjust the titer of one out of the two after the storage and before filling, to facilitate the manufacturing process by separation of the two products drying.

SUMMARY OF THE INVENTION

The present invention provides a process for stabilizing an adjuvant containing vaccine composition comprising the steps of diluting a liquid bulk composition comprising an antigen or an antigenic preparation by an aqueous solution comprising a stabilizer, subjecting the diluted composition to a process in order to form regular droplets having a diameter of approximately from about 200 μm to about 1500 μm, subjecting the regular droplets to freezing in a freezing medium to form frozen regular spherical micropellets or particles and drying the frozen regular spherical micropellets or particles to form dry regular spherical micropellets or particles having a diameter from about 200 μm to about 1500 μm.

BRIEF DESCRIPTION OF THE DRAWING(S)

FIG. 1. illustrates the general formulation and drying procedure.

FIG. 2. illustrates the process used to generate the dry micropellets, including prilling, freezing, drying and filling.

FIG. 3. illustrates the general formulating, freezing and drying procedure comprising an adjuvant.

FIG. 4. illustrates the formulation and drying procedure to produce the antigen containing micropellets, FIG. 5. illustrates the formulation and drying procedure to produce the adjuvant containing micropellets.

FIG. 6. illustrates the procedure for the combination of the different micropellets in order to complete the dry vaccine.

FIG. 7. illustrates the formulation and drying procedure as described in Example 1.

FIG. 8. shows the narrow size distribution of the micropellets obtained with pelletizing and drying technology as described in Example 1.

FIG. 9. shows the size distribution results after drying of an aluminum phosphate gel in presence of a carbohydrate and using the micropellet technology. Size distribution of the aluminum phosphate gel before drying (black curve, right) and after drying in micro-pellet form and rehydration (grey curve, left). No sign of aggregation was observed. DLS measurements.

FIG. 10. illustrates the formulation and drying procedure as described in Example 2.

FIG. 11. shows the aluminum oxyhydroxide gel particle size distribution in the formulated bulk before drying and after dissolution of the pellets.

FIG. 12. shows the aluminum oxyhydroxide gel particle size distribution after thermostability incubation for at least 7 days at 37° C., 45° C. and 55° C.

FIG. 13. illustrates the formulation and drying procedure as described in Example 3.

FIG. 14. shows a comparison of the size of the emulsion before rehydration of the micropellets and after dissolution of the micropellets. Comparison of the size of the emulsion before rehydration of the micropellets (solid line curve) and after dissolution of the micropellets (dashed line curve).

FIG. 15. shows the stability of the size of the emulsion after dissolution of the micropellets and over a one hour storage period at room temperature. Stability of the size of the emulsion at room temperature after dissolution of the micropellets. Exact superposition of size distribution curves of the emulsion right after dissolution and 7, 15, 30, 45 and 60 min after dissolution.

FIG. 16. illustrates the formulation and drying procedure as described in Example 4a.

FIG. 17. illustrates the formulation and drying procedure of the formulations containing *Diphtheria* toxoid and *Tetanus* toxoid in presence of aluminum gel as described in Example 5.

FIG. 18. illustrates the formulation and drying procedure of the formulations containing *Diphtheria* toxoid and *Tetanus* toxoid without aluminum gel as described in Example 5.

FIG. 19. illustrates the formulation and drying procedure of aluminum gel formulation as described in Example 5.

DETAILED DESCRIPTION OF THE INVENTION

Suitable vaccine compositions are for example compositions comprising whole viruses or antigens, such as Influenza, Rotavirus, cytomegalo virus, Hepatitis A and B, whole bacteria or bacterial protein or polysaccharide antigens (conjugated or non-conjugated), such as *Haemophilus influenzae*, meningococcal polysaccharides, *Tetanus, Diphteria*, cellular and acellular pertussis, Botulism, Anthrax or *C. Difficile*.

The freezing of the droplets can e.g. be achieved in that the diluted composition, i.e. the formulated liquid product, is prilled in order to generate calibrated droplets which diameter ranges from 200 μm to 1500 μm, with a very narrow size distribution. These droplets fall in a cryogenic chamber in which the temperature is maintained below −110° C. by a freezing medium, either by direct injection/nebulization of liquid nitrogen or by flowing counter currently a very cold (T°<−110° C.) gas such as nitrogen, $CO_2$ or air. The droplets freeze during their fall in order to form calibrated frozen particles.

Other techniques are known in the art for obtaining calibrated droplets, such as ultrasonic atomization (Sindayihebura D., Dobre M., Bolle L., 1997—Experimental study of thin liquid film ultrasonic atomization. ExHFT'97, Bruxelles.), and, subsequently, calibrated frozen particles or, as mentioned before being known from the food industry, by means of a particular freezing drum as disclosed in U.S. Pat. No. 5,036,673.

The process may further comprise the addition of an aqueous solution comprising one or more adjuvants and, optionally, a stabilizer to the liquid bulk antigen composition.

Alternatively, the process according to the present invention further comprises diluting a separate liquid bulk solution or emulsion of one or more adjuvants by an aqueous solution comprising a stabilizer, subjecting the diluted adjuvant solution or emulsion to a process in order to form regular droplets having a diameter of approximately from about 200 μm to about 1500 μm, subjecting the regular droplets to freezing in a freezing medium to form frozen regular spherical micropellets or particles, drying the frozen regular spherical micropellets or particles to form dry regular spherical micropellets or particles having a diameter from about 200 μm to about 1500 μm and blending and filling into a vial or other appropriate container together with the antigen containing dry regular spherical micropellets.

The liquid bulk composition may further comprise one or more additional antigens or antigenic preparations, each from a different pathogen or serotype of a pathogen, in order to obtain dry regular spherical micropellets or particles, each comprising two or more antigens or antigenic preparations from two or more different pathogens or serotypes of a pathogen.

Alternatively, the liquid bulk composition comprises an antigen or antigenic preparation from one single pathogen or serotype of a pathogen, in order to obtain dry regular spherical micropellets or particles, each comprising antigens or antigenic preparations from the same pathogen or serotype of a pathogen. In this case the process may optionally further comprise the dosing, blending and filling into a vial or other appropriate container two or more types of dry regular spherical micropellets or particles, characterized in that each type of micropellets comprises antigens or antigenic preparations from two or more different pathogens or serotypes of a pathogen.

The process according to the present invention may be further characterized in that the drying occurs by the method of lyophilization (i.e. sublimation of ice and dissorption of bound water). Suitable drying methods are also atmospheric freeze-drying, fluidized bed drying, vacuum rotary drum drying, stirred freeze-drying, vibrated freeze-drying and microwave freeze-drying.

Advantageously, the stabilizer comprises a monosaccharide, such as mannose, an oligosaccharide, such as sucrose, lactose, trehalose, maltose or a sugar alcohol, such as sorbitol, mannitol or inositol, or a mixture of two or more different of these before mentioned stabilizers, such as mixtures of sucrose and trehalose.

Advantageously, the concentration of carbohydrates, sugar alcohols and stabilizing excipients ranges from 2% (w/v) to limit of solubility in the formulated liquid product. In general, the concentration of carbohydrates, sugar alcohols and stabilizing excipients ranges between 5% (w/v) and 40% (w/v), 5% (w/v) and 20% (w/v) or 20% (w/v) and 40% (w/v). Examples for the concentration of a 1:1 mixture of sucrose and trehalose in the formulated liquid product comprising e.g. *tetanus* or *diphtheria* toxoids and aluminum gel (AlOOH) are 18.1% (w/v) and 17.5% (w/v), respectively.

The present invention particularly relates to a process for stabilizing an influenza vaccine composition comprising the steps of diluting a liquid bulk composition comprising an influenza antigen or an antigenic preparation from a seasonal, pre-pandemic or pandemic influenza virus strain by an aqueous solution comprising a carbohydrate and/or a sugar alcohol or a mixture of two or more different carbohydrates and/or sugar alcohols in order to obtain a 2% (w/v) to limit of solubility of carbohydrate and/or sugar alcohol content of the resulting diluted composition, subjecting the diluted composition to a process in order to form regular droplets having a diameter of approximately from about 200 µm to about 1500 µm, subjecting the regular droplets to freezing in a freezing medium to form frozen regular spherical micropellets or particles and drying the frozen regular spherical micropellets or particles to form dry regular spherical micropellets or particles having a diameter from about 200 μm to about 1500 μm.

The liquid bulk composition comprising an influenza antigen or an antigenic preparation from a seasonal, pre-pandemic or pandemic influenza virus strain can be obtained by the method as disclosed in U.S. Pat. No. 6,048,537 (WO 96/05294).

The drying occurs advantageously by the method of lyophilization (i.e. sublimation of ice and dissorption of bound water). Further suitable drying methods for the frozen micropellets are atmospheric freeze-drying, fluidized bed drying, vacuum rotary drum drying, stirred freeze-drying, vibrated freeze-drying, and microwave freeze-drying.

Advantageously, the carbohydrate is a disaccharide, particularly sucrose. Also suitable disaccharides are for example lactose, maltose or trehalose. Also suitable for stabilizing the influenza vaccine composition are monosaccharides, such as mannose, or sugar alcohols, such as sorbitol, inositol or mannitol.

Advantageously, the concentration of the carbohydrates or sugar alcohols ranges between 5% and 40% (w/v), alternatively between 5% and 20% (w/v) or between 20% and 40% in the formulated liquid product. Examples for the concentrations of e.g. sucrose in the formulated liquid product are 2% (w/v), 10% (w/v) or 15.4% (w/v).

The liquid bulk composition may further comprise one or more additional influenza antigens or antigenic preparations, each from a different seasonal, pre-pandemic or pandemic influenza virus strain, in order to obtain dry regular spherical micropellets or particles, each comprising two or more influenza antigens or antigenic preparations from two or more different seasonal, pre-pandemic or pandemic influenza virus strains. In this case the process optionally further comprises dosing and filling the dry regular spherical micropellets or particles into a vial or other appropriate container.

Alternatively, the liquid bulk composition comprises one or more influenza antigens or antigenic preparations from one seasonal, pre-pandemic or pandemic influenza virus strain, in order to obtain dry regular spherical micropellets or particles, each comprising influenza antigens or antigenic preparations from the same seasonal, pre-pandemic or pandemic influenza virus strain. In this case the process may optionally further comprise dosing, blending and filling into a vial or other appropriate container two or more types of dry regular spherical micropellets or particles, characterized in that each type of micropellets comprises influenza antigens or antigenic preparations from a different seasonal, pre-pandemic or pandemic influenza virus strain than the other type.

The process optionally further comprises the addition of an aqueous solution comprising one or more adjuvants and, optionally, a stabilizer to the liquid bulk antigen composition.

Alternatively, the process according to the present invention further comprises diluting a separate liquid bulk solution or emulsion of one or more adjuvants by an aqueous solution comprising a stabilizer, subjecting the diluted adjuvant solution or emulsion to a process in order to form regular droplets having a diameter of approximately from about 200 μm to about 1500 μm, subjecting the regular droplets to freezing in a freezing medium to form frozen regular spherical micropellets or particles, drying the frozen regular spherical micropellets or particles to form dry regular spherical micropellets or particles having a diameter from about 200 μm to about 1500 μm and blending and filling into a vial or other appropriate container together with the antigen containing dry regular spherical micropellets.

Particularly suitable adjuvants are for example liposomes, lipid or detergent micellles or other lipidic particles, polymer nanoparticles or microparticles, soluble polymers, protein particles, mineral gels, mineral micro- or nanoparticles, polymer/aluminum nanohybrids, oil in water or water in oil emulsions, saponin extracts, bacterial cell wall extracts, stimulators of innate immunity receptors, in particular natural or synthetic TLR agonists, natural or synthetic NOD agonists and natural or synthetic RIG agonists. A suitable adjuvant for the process according to the present invention for example is that disclosed in WO 2007/006939.

The influenza virus strains are for example H5N1, H9N2, H7N7, H2N2, H7N1 and H1N1 (Emergence of multiple genotypes of H5N1 avian influenza viruses in Hong Kong SAR: Y Guan et al., 8950-8955, PNAS—Jun. 25, 2002—vol 99 n° 13; H9N2 Influenza A Viruses from Poultry in Asia have Human Virus-like Receptor Specificity: MN Matrosovich, S Krauss and R Webster, Virology 281, 156-162 (2001); Evolution and Ecology of Influenza A Viruses: R Webster et al., Microbiological ReviewsMar 1992, p. 152-179). Alternatively, it could be an influenza strain selected from the group of the seasonal influenza virus strains.

The influenza antigen can be in a form selected from the group consisting of purified whole influenza virus, inactivated influenza virus or sub-unit components of influenza virus, or a split influenza virus.

The influenza antigen may be derived from cell culture. Alternatively, the influenza antigen is produced in embryonic eggs.

The present invention also concerns a stabilized dry vaccine composition, particularly a stabilized dry influenza vaccine composition or stabilized dry vaccine compositions containing other antigens, such as inactivated whole viruses or antigenic components of viruses, Influenza, Rotavirus, cytomegalo virus and Hepatitis A and B, and whole bacteria or bacterial protein or polysaccharide antigens, conjugated or non-conjugated, such as *Haemophilus influenzae*, meningococcal polysaccharides, *tetanus, diphtheria*, cellular and acellular pertussis, Botulism, Anthrax, *C. Difficile* in the form of dry regular spherical micropellets or particles having a diameter from about 200 μm to about 1500 μm obtainable by the process according to the present invention.

Advantageously, each regular bead or particle comprises only one type of antigen, for example one or more influenza antigens from only one influenza virus strain or for example only *Tetanus* or only *Diphtheria* antigens. Alternatively, each regular bead or particle comprises one or more types of antigens, for example influenza antigens from one or more different influenza virus strains or for example *Tetanus* and *Diphtheria* antigens.

The composition may further comprise an adjuvant which is optionally contained in separate dry regular spherical micropellets or particles.

The present invention further relates to a process for the preparation a vaccine comprising the step of reconstitution of the stabilized dry vaccine composition, for example the before mentioned stabilized dry influenza vaccine composition in the form of dry regular spherical micropellets or particles in an aqueous solution. The aqueous solution may optionally comprise an adjuvant.

The present invention further relates to a vaccine kit, comprising a first container containing a stabilized dry vaccine composition, for example a stabilized dry influenza vaccine composition, in the form of dry regular spherical micropellets or particles and a second container containing an aqueous solution for the reconstitution of the vaccine. The kit may further comprise a container containing dry regular spherical micropellets or particles comprising an adjuvant. Alternatively, the aqueous solution comprises an adjuvant.

The present invention also relates to a method of stockpiling a stable dry bulk of antigens wherein the antigen or the antigens is/are stabilized by the method described before and the resulting stabilized dry vaccine composition (e.g. an influenza, *diphtheria* or *tetanus* vaccine composition) is reconstituted with an adequate solvent and optionally formulated prior to liquid filling into vials or syringes after storage in the form of dry regular spherical micropellets or particles having a diameter from about 200 μm to about 1500 μm.

The process for thermo-stabilization of dry vaccine in micro-pellet form according to the present invention is explained in more detail in the following.

In order to be processed by the micro-pellet technology, biological substances such as antigens require to be formulated in order to protect it against the physical and chemical stresses undergone throughout the process.

Formulated liquid products to be dried are obtained by mixing the concentrated vaccine bulk (containing the antigen) and a stabilizing formulation comprising at least one carbohydrate and/or sugar alcohol, so that the formulated liquid product obtained contains the targeted amounts per ml of stabilizing excipients and antigens. The concentration of carbohydrates, sugar alcohols and stabilizing excipients ranges between 2% (w/v) to limit of solubility in the formulated liquid product. To give an example, the concentration at the limit of solubility of sucrose in water at 20° C. is at about 66.7% (w/v).

FIG. 1 shows a flow chart of the general formulation and drying procedure.

Figure 2:
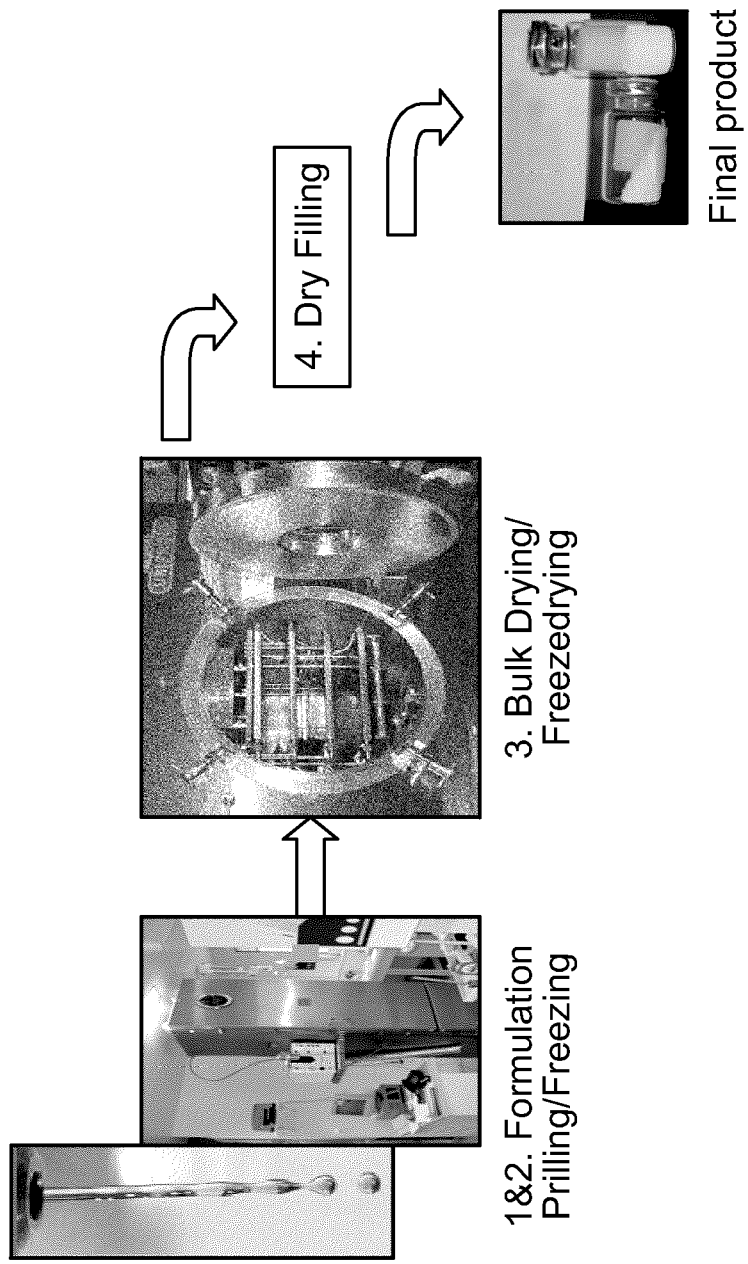

The process as shown in FIG. 2 is used to generate the dry micropellets.

Prilling, also known as laminar jet break-up technique, is a well known technique to generate calibrated droplets of liquid commonly used in the field of biocatalysts and living cells immobilization (Hulst et al., 1985. A new technique for the production of immobilized biocatalyst and large quantities. Biotechnol. Bioeng. 27, 870-876; Gotoh et al., 1993. Mass production of biocatalyst-entrapping alginate gel particles by a forced oscillation method. Chem. Eng. Commun. 120, 73-84.; Seifert and Philips, 1997. Production of small, monodispersed alginate beads for cell immobilization. Biotechnol. Prog. 13, 562-568). Lord Rayleigh was the first to analyze instability of capillary jets coming out of a nozzle and to propose a model to describe it (Rayleigh L, 1978. On the stability of jets. Proc. London Math. Soc. 10, 4-13) for Newtonian fluids. Weber (Weber C, 1931. Zum Zerfall eines Flüssigkeitsstrahles. Z. Angew. Math. Mech. 11, 136-154) extended the analysis including the effect of the viscosity. The optimal wavelength for the fastest growing disturbance and jet beak-up is given by:

$$\lambda_{opt} = \pi \cdot \sqrt{2} \cdot d_j \cdot \sqrt{1 + \frac{3\eta}{\sqrt{\rho \sigma d_j}}}$$

where $\lambda_{opt}$ is the optimal wave-length for jet break-up, $d_j$ is the diameter of the jet, $\eta$ is the viscosity of the fluid, $\rho$ is the density of the fluid and $\sigma$ is the surface tension of the fluid. The diameter d of the droplets formed can be calculated by:

$$d = \sqrt[3]{1.5 \cdot d_j^2 \cdot \lambda_{opt}}$$

The frequency f to apply to the fluid to achieve the desired results is related to the jet velocity (and therefore the flow rate of the fluid) $u_j$ and the wavelength by:

$$\lambda = \frac{u_j}{f}$$

Therefore; optimal conditions can be calculated knowing process parameters and fluid characteristics. However, a range of frequencies and jet velocities exist to form uniform droplets depending on the nozzle diameter, rheology of the fluid and surface tension (Meesters G., 1992. Mechanisms of droplet formation. Delft University Press, Delft, NL). Suitable working frequencies can be also be determined experimentally by visual assessment of the stability of the droplet formation. Standard prilling equipments are equipped with light stroboscope to observe the droplet formation: for a given product and given working conditions, one can adjust manually the frequency until observing a stable and still droplets chain with this stroboscope light.

Moreover, multinozzle systems have been developed for aseptic prilling applications (Brandenberger H. et all 998. A new multinozzle encapsulation/immobilization system to produce uniform beads of alginates. J. Biotechnol. 63, 73-80)

In conclusion, working frequencies can be determined both theoretically and experimentally depending on the available tools and knowledge of the product.

The prilling process is adapted to viscous liquids and saturated sugar solutions. The maximum acceptable viscosity according to current suppliers is approximately 300 mPa·s. Therefore, formulation content can range from very low concentration up to the limit of solubility of the selected excipients at room or processing temperature. Moreover, the temperatures in the process tubing and in the nozzle have to be controlled in order to avoid sugar or solvent crystallization before droplet formation. The person skilled in the art of formulation will adjust different excipient concentrations in the product in order to avoid non-controlled crystallization and viscosities above the given limit, taking into account eventual interactions between excipients.

The formulated liquid product is prilled in order to generate calibrated droplets the diameter of which ranges from 200 μm to 1500 μm, with a very narrow size distribution. These droplets fall in a cryogenic chamber in which temperature is maintained below −110° C. either by direct injection/nebulization of liquid nitrogen or by flowing counter currently a very cold (T°<−110° C.) gas such as nitrogen, $CO_2$ or air. The droplets freeze during their fall in order to form calibrated frozen particle. The minimum falling height to freeze the droplets (i.e. ice crystals formation that solidifies the pellets) can be minimized by limiting super-cooling. Super-cooling can be reduced by seeding ice nucleation in the droplets either by contact with liquid nitrogen fog or droplets (direct injection of liquid nitrogen in the chamber) or with microscopic ice crystals (direct nebulization of water or superheated steam in the cold chamber).

These frozen particles are then collected and transferred on pre-cooled trays at −50° C. and loading on the pre-cooled shelves of the freeze-drier (−50° C.) in order to always keep the frozen pellets below the glass transition Tg' of their cryo-concentrated phase (Tg' value can range from −10° C. to −45° C.) and to avoid any melting or aggregation of the particles. Once the freeze-drier is loaded, vacuum is pulled in the freeze-drying chamber to initiate conventional freeze-drying (sublimation of the ice) of the pellets as know by the state of the art. The following freeze-drying parameters are an example of what can be used for a formulation which Tg' ranges from −30° C. to −45° C.:

Primary drying: shelf temperature equal to −35° C., pressure equal to 50 μbars during 10 h.

Secondary drying: shelf temperature equal to 20° C., pressure equal to 50 μbars during 3 h.

Freeze-drying cycle has to be designed in order to get residual moistures preferentially lower than 3%. However, the moisture content can be optimized at higher value, on a case by case basis, if the stability of the dry antigen requires it.

Other drying technologies such as atmospheric freeze-drying, fluidized bed drying, vacuum rotary drum drying, stirred freeze-drying, vibrated freeze-drying, microwave freeze-drying can be used to dry the pellets.

Dry pellets are then collected in bulk to be analyzed and stored. Storage conditions are suitable for dry, friable and hygroscopic particles. Dry samples are rehydrated prior to analysis using a diluent which may contain water for injection, buffers, stabilizing excipients and adjuvants. Dissolution is instantaneous.

Bulk dry pellets are then filled into vials using dry powder filling technologies that are currently on the market.

Also, in a perspective of stockpiling a stable dry bulk of antigen, the pellets can be reconstituted with adequate solvent and formulated (if needed) prior to liquid filling into vials or into syringes. Thanks to the stability of such pellets, the storage of the stockpile can be performed at +5° C. or higher temperatures, which is more convenient than for a frozen liquid material (−20° C. or lower). Finally, stockpiling dry bulk material is much less space consuming than stockpiling filled dry products in their final container.

In the case of adjuvanted vaccine, the stability during storage at +5° C. or higher and lower (freezing) temperature is often a problem when antigens and adjuvants are in the same liquid state. As an example, the table below describes the impact of a freeze-thawing cycle at −20° C. on oxyhydroxyl aluminum gel measured by dynamic light scattering:

| | Particles size (μm) | | | |
|---|---|---|---|---|
| | mean | d10 | d50 | d90 |
| Initial +5° C. | 8.9 | 2.6 | 4.9 | 10.3 |
| 1 freeze-thawing cycle −20° C. | 49.6 | 15.3 | 43.7 | 92.4 |

The micropellet technology allows overcoming stability problems with 3 different strategies to be selected on a case by case basis:

1. Drying of the antigens alone under micropellet form and dissolution with the adjuvant (aluminum gel, emulsion, etc.) in the diluent. This strategy is suitable when the antigen stability is increased under micropellet form and when the adjuvant alone is highly thermostable No interaction during shelf life Increased stability of each phase when stored independently Standardization of adsorption behavior by extemporaneous dissolution of the dry antigen with the liquid adjuvant 2. Drying of the antigens with the adjuvant to stabilize both within the same pellet and to stabilize the interaction between them by trapping them in a glassy matrix in which all molecular motions and chemical reactions are greatly hindered. This solid state allows to maintain throughout storage (even at higher temperature) potency of the antigen, physical and immunological properties of the adjuvant and nature and force of the interaction between the two.

3. Drying of the antigens and the separate drying of the adjuvant, followed by blending of the two before the filling or by a sequential filling. In some cases, stability of the adjuvant alone can be a problem (chemical stability of emulsions, physical stability of aluminum gels, liposomes and others . . . ) at the liquid state for long term storage at +5° C. or higher temperatures. The micropellet technology allows improving stability of the adjuvanted vaccine by generating separate micropellets of antigen and adjuvant. Stabilizing formulation can be optimized independently for each antigens and the adjuvant. micropellets of antigens and adjuvants can be then subsequently filled into the vials. The separated solid state allows to avoid throughout storage (even at higher temperature) interactions between antigen and adjuvant, to maintain potency of the antigen and physical and immunological properties of the adjuvant. In such a configuration, the content of the vial is more stable than any other configurations with either one of the antigens or in the adjuvant in the liquid state or when antigens and adjuvant are dried within the same pellets. Interactions between antigens and adjuvants are this way standardized as they occur only after rehydration of the dry combination with a selected diluent which may comprise water for injection, buffers and stabilizing excipients. Interactions therefore exist only during the short period of time between rehydration and injection of the vaccine (fast interactions and very short aging time). It is therefore possible to improve the overall stability of the two products (optimization of the formulation for each product and not a compromise for the two together) and the vaccine itself, adjust the titer of one out of the two after the storage, to facilitate the manufacturing process by separation of the two products drying.

In order to be processed by the micropellet technology, biological substances such as antigens and adjuvants require to be formulated in order to protect them against the physical and chemical stresses undergone throughout the process.

In case of adjuvants, the stabilizing formulation has to maintain their quality during processing (formulation, pelletizing, drying, storage, filling and rehydration)

If the strategy is to dry both antigens and adjuvants in the same micro-pellet, formulated liquid product to be dried is obtained by mixing the concentrated vaccine bulk (containing the antigens), the concentrated adjuvant bulk and a stabilizing formulation comprising at least one carbohydrate and or sugar alcohol, so that the formulated liquid product obtained contains the targeted amounts per ml of stabilizing excipients, adjuvants and antigens. The concentration of the stabilizing excipients ranges between 2% (w/v) and limit of solubility in the formulated liquid product.

Figure 3:
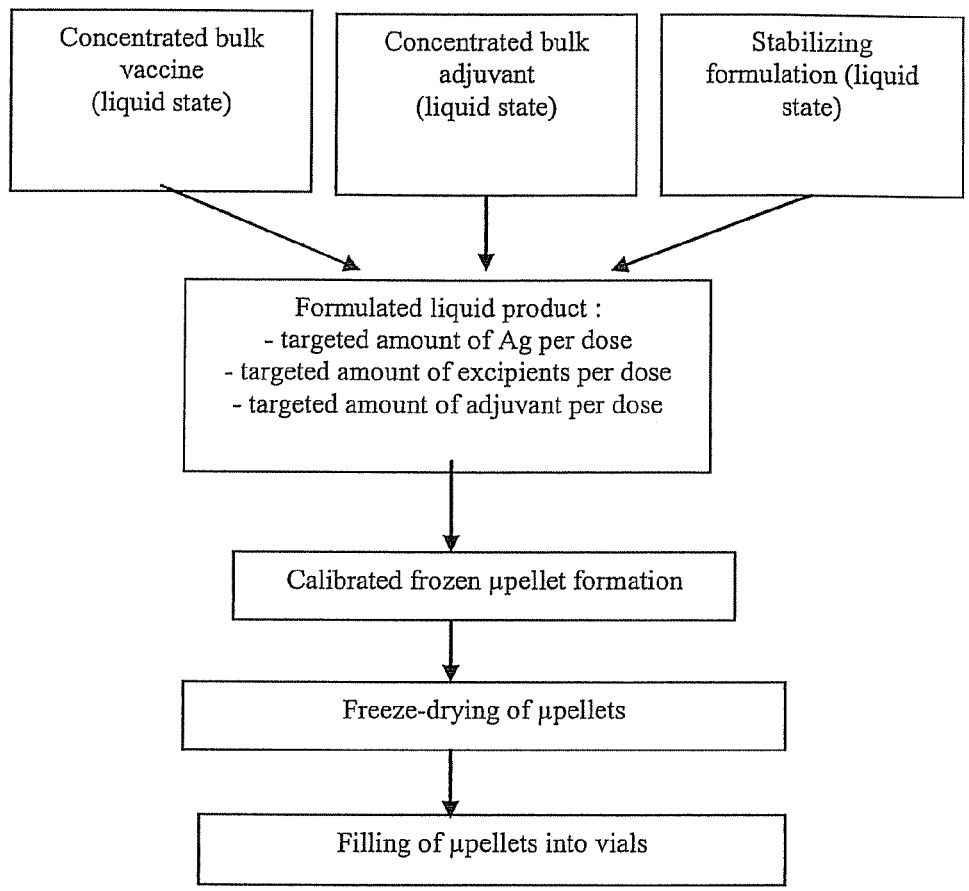

FIG. 3 is a flow chart showing the formulation and drying procedure comprising an adjuvant.

If the strategy is to dry antigens and adjuvants in separate micropellets, the formulated liquid product to be dried (comprising the antigens) is obtained by mixing the concentrate vaccine bulk (comprising the antigens) and a stabilizing formulation, so that the formulated liquid product obtained contains the targeted amounts per ml of stabilizing excipients and antigens. The concentration of the carbohydrates and the stabilizing excipients ranges between 2% (w/v) and limit of solubility in the formulated liquid product.

The same way for the adjuvant, the formulated liquid product to be dried is obtained by mixing the concentrated adjuvant bulk and a stabilizing formulation, so that the formulated liquid product obtained contains the targeted amounts per ml of stabilizing excipients and adjuvants. The carbohydrates and stabilizing excipients concentration ranges are between 2% (w/v) and limit of solubility in the formulated liquid product.

Figure 5:
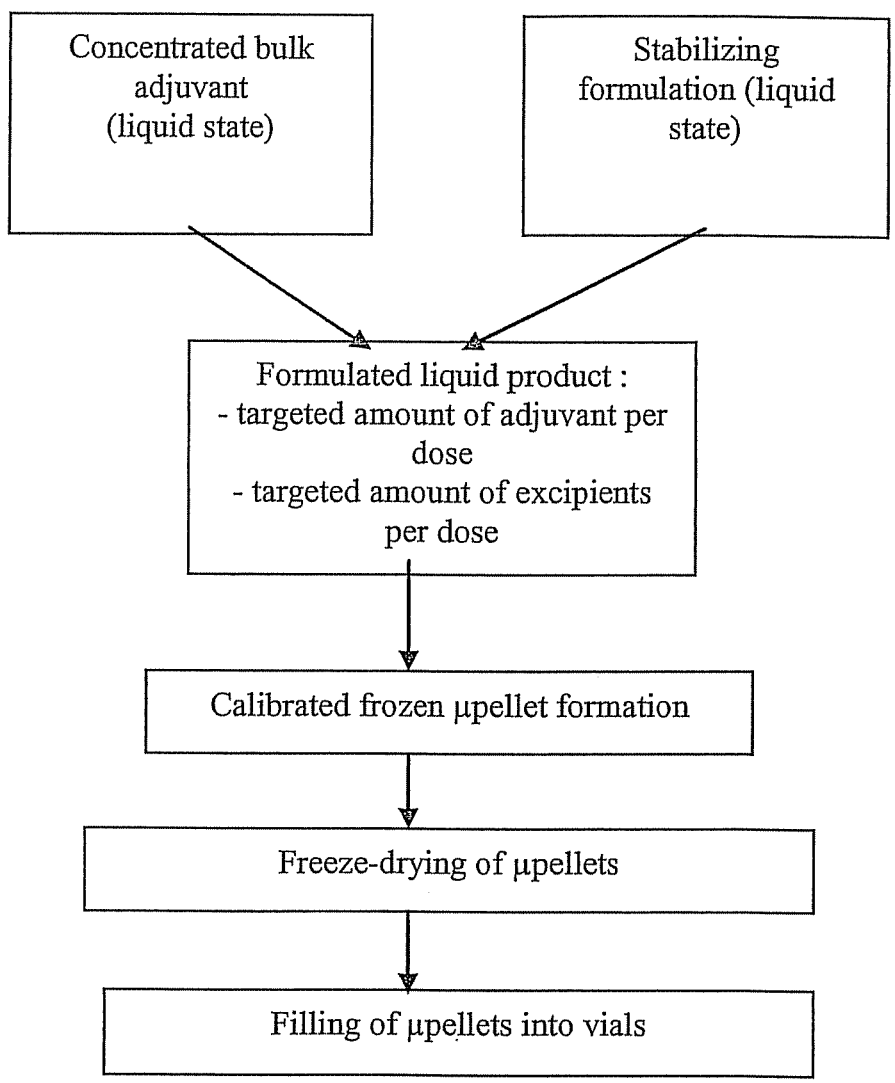
Figure 6:
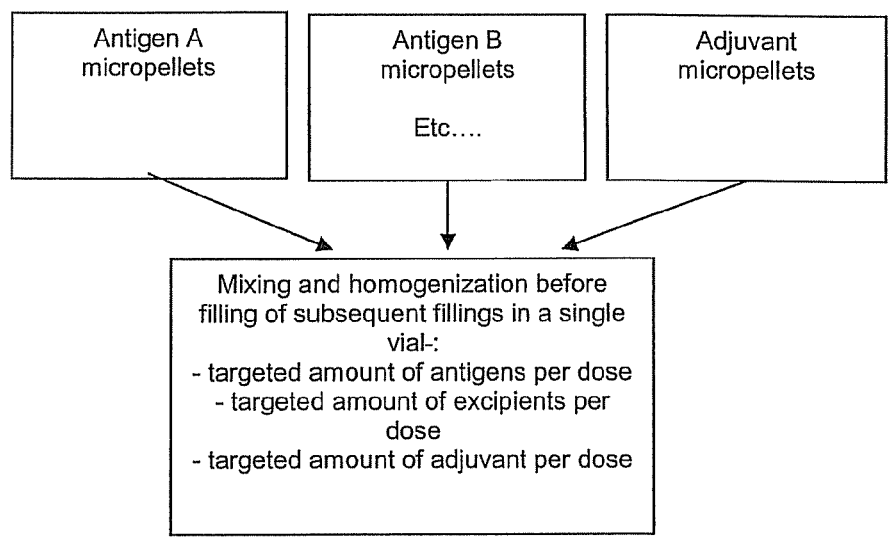
Figure 7:
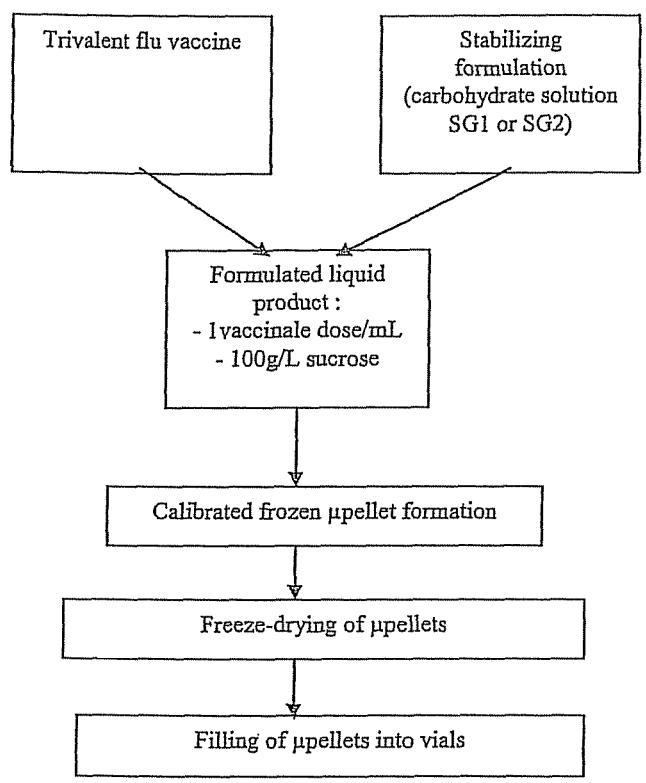
Figure 8:
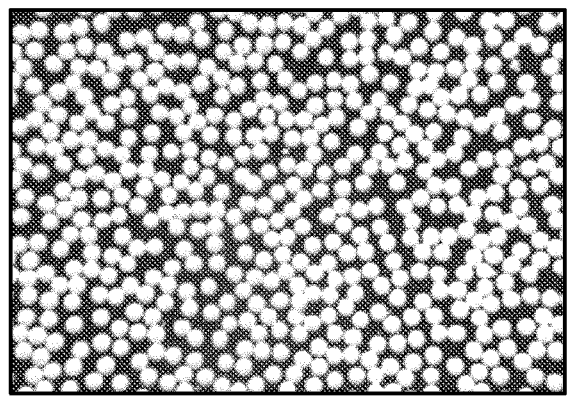

FIG. 4 is a flow chart showing the formulation and drying procedure in order to produce the antigen containing micropellets, FIG. 5 is a flow chart showing the formulation and drying procedure in order to produce the adjuvant containing micropellets. FIG. 6 shows the combination of the different micropellets in order to complete the dry vaccine.

The general process for the generation of the dry micropellets is shown in FIG. 2. It is applicable independently from the chosen strategy for the adjuvanted vaccine.

Figure 9:
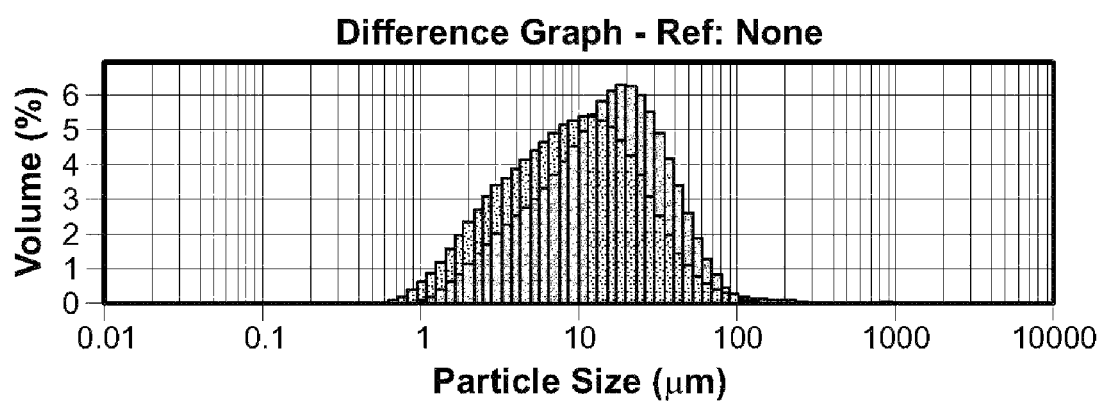

Fast freezing kinetics of the micro-pellet technology is also adapted for drying adjuvants. As an example, the graph in FIG. 9 shows size distribution results after drying of an aluminum phosphate gel in presence of a carbohydrate and using the micro-pellet technology. It can be seen that drying and rehydration has no significant negative effect on the size distribution of the adjuvant particles.

Suitable adjuvants that may be considered are exemplified in the following:

1) The particulate adjuvants such as: liposomes and in particular cationic liposomes (e.g. DC-Chol, see e.g. US 2006/0165717, DOTAP, DDAB and 1,2-Dialkanoyl-sn-glycero-3-ethylphosphocholin (EthylPC) liposomes, see U.S. Pat. No. 7,344,720), lipid or detergent micelles or other lipid particles (e.g. Iscomatrix from CSL or from Isconova, virosomes and proteocochleates), polymer nanoparticles or microparticles (e.g. PLGA and PLA nano- or microparticles, PCPP particles, Alginate/chitosan particles) or soluble polymers (e.g. PCPP, chitosan), protein particles such as the *Neisseria meningitidis* proteosomes, mineral gels (standard aluminum adjuvants: AlOOH, AlPO$_4$), microparticles or nanoparticles (e.g. Ca$_3$(PO$_4$)$_2$), polymer/aluminum nanohybrids (e.g. PMAA-PEG/AlOOH and PMAA-PEG/AlPO$_4$ nanoparticles) O/W emulsions (e.g. MF59 from Novartis, AS03 from GlaxoSmithKline Biologicals) and W/O emulsion (e.g. ISA51 and ISA720 from Seppic, or as disclosed in WO 2008/009309). For example, a suitable adjuvant emulsion for the process according to the present invention is that disclosed in WO 2007/006939.

2) The natural extracts such as: the saponin extract QS21 and its semi-synthetic derivatives such as those developed by Avantogen, bacterial cell wall extracts (e.g. micobacterium cell wall skeleton developed by Corixa/GSK and micobaterium cord factor and its synthetic derivative, trehalose dimycholate).

3) The stimulators of innate immunity receptors such as: natural or synthetic TLR agonists (e.g. synthetic lipopeptides that stimulate TLR2/1 or TLR2/6 heterodimers, double stranded RNA that stimulates TLR3, LPS and its derivative MPL that stimulate TLR4, E6020 and RC-529 that stimulate TLR4, flagellin that stimulates TLR5, single stranded RNA and 3M's synthetic imidazoquinolines that stimulate TLR7 and/or TLR8, CpG DNA that stimulates TLR9, natural or synthetic NOD agonists (e.g. Muramyl dipeptides), natural or synthetic RIG agonists (e.g. viral nucleic acids and in particular 3' phosphate RNA).

These adjuvants may also be used in combination. Preferred combinations are those between the particulate adjuvants and natural extracts and those between particulate adjuvants and stimulators of innate immunity receptors.

For the following examples, the prilling apparatus IE-50R Encapsulator Research, from Inotech (CH) and a 300 μm nozzle head were used to generate the micropellets.

EXAMPLE 1

Manufacturing of Thermo-Stable Dry Vaccine Under Micropellet Form Containing Flu Antigens This study compared the thermo-stability of the current liquid trivalent flu vaccine to dry formulations of this same vaccine processed with the micro pellet technology. Trivalent flu vaccine contains 30 µg/ml of each A/Salomon, B/Malaysia and A/Wisconsin strains in the vaccinal buffer. Formulated liquid products to be dried were obtained by mixing one volume of trivalent flu vaccine with one volume of a stabilizing formulation comprising at least one carbohydrate which concentration ranges between 4% (w/v) and limit of solubility. This corresponds to a concentration range from 2% to 32% (weight by volume) in the formulated liquid product to be dried. Two formulations were evaluated: SG1 and SG2 which compositions are given in tables 1 and 2:

TABLE 1

| SG1 | |
|---|---|
| COMPONENTS | |
| quantity for | 1000 ml |
| Sucrose | 200 g |
| Adjustment pH @ 7.0 +/− 0.2 (NaOH, HCl) | |
| Water PPI | 1000 ml |

TABLE 2

| SG2 | |
|---|---|
| COMPONENTS | |
| quantity for | 1000 ml |
| Sucrose | 200 g |
| Glutamine | 2 g |
| Urea | 10 g |
| Dextrane 70 | 10 g |
| Adjustment pH @ 7.0 +/− 0.2 (NaOH, HCl) | |
| Water PPI | 1000 ml |

FIG. 7 shows a flowchart of the formulation and drying procedure.

FIG. 2 shows the process that was used to generate the dry micropellets of formulations SG1 and SG2.

Formulated liquid product SG1 and SG2 were prilled in order to generate calibrated droplets. Prilling parameters for this formulation and a 300 μm nozzle head were:

Product flow rate: 8 ml/min nozzle frequency: 954 Hz

These droplets fell in a cryogenic chamber in which the temperature was maintained below −110° C. by direct injection of liquid nitrogen or by flowing countercurrent very cold gas (t°<−110° C.). The droplets froze during their fall and formed calibrated frozen particles.

These frozen particles were then transferred on pre-cooled trays at −50° C. and loaded on the pre-cooled shelves of the freeze-drier (−50° C.) in order to always keep the frozen pellets below their glass transition (which was evaluated between −30° C. and −40° C.) and to avoid any melting or aggregation of the particles. Once the freeze-dryer was loaded, vacuum was pulled in the freeze-drying chamber to initiate conventional freeze-drying of the pellets as know by the state of the art. For these formulations, the following freeze-drying parameters were used: Primary drying: shelf temperature equal to −35° C., pressure equal to 50 μbars during 10 h. Secondary drying: shelf temperature equal to 20° C., pressure equal to 50 μbars during 3 h. Residual moisture of the micropellets was below 2% for both SG1 and SG2 formulations.

FIG. 8 gives an idea of the very narrow size distribution obtained with this pelletizing and drying technology.

Therefore, 3 products were available for a thermo-stability study: The marketed trivalent flu vaccine (VAXIGRIP®, Sanofi Pasteur), the dry micropellets SG1 formulation (trivalent flu vaccine) and the dry micropellets SG2 formulation (trivalent flu vaccine).

Samples of each of these 3 formulations were exposed to different time at 37° C. and 45° C. Potency (μg of antigen/ml) was then measured for each sample by SRD (SRID) method (M. S. Williams, Veterinary Microbiology, 37 (1993) 253-262). Dry samples were re-hydrated using water for injection prior to analysis. Dissolution was instantaneous. The tables 3, 4 and 5 summarize the obtained results. Results are expressed in mean value μg/ml of antigen.

TABLE 3

| A/Salomon | | | | |
|---|---|---|---|---|
| | Stability at 37° C. (days) | | | |
| | 0 | 7 | 30 | 90 |
| Liquid formulation | 29.8 | 24.3 | | 12.1 |
| micropellets SG1 | 23.2 | 22.5 | 24.9 | 27 |
| micropellets SG2 | 26.5 | 24.7 | 28.2 | 29.4 |
| | Stability at 45° C. (days) | | | |
| | 0 | | 7 | |
| Liquid formulation | 29.8 | | 16.4 | |
| micropellets SG1 | 23.2 | | 24.3 | |
| micropellets SG2 | 26.5 | | 25.8 | |

TABLE 4

| B/Malaysia | | | | |
|---|---|---|---|---|
| | Stability at 37° C. (days) | | | |
| | 0 | 7 | 30 | 90 |
| Liquid formulation | 30 | 21.4 | | 14.4 |
| micropellets SG1 | 25.4 | 25.7 | 24.9 | 28.2 |
| micropellets SG2 | 26.6 | 25.4 | 27.2 | 30.4 |
| | Stability at 45° C. (days) | | | |
| | 0 | | 7 | |
| Liquid formulation | 30 | | 16.3 | |
| micropellets SG1 | 25.4 | | 24 | |
| micropellets SG2 | 26.6 | | 26.7 | |

TABLE 5

| A/Wisconsin | | | | |
|---|---|---|---|---|
| | Stability at 37° C. (days) | | | |
| | 0 | 7 | 30 | 90 |
| Liquid formulation | 30 | 24.7 | | 13.2 |
| micropellets SG1 | 25.4 | 24.6 | 25.5 | 26.8 |
| micropellets SG2 | 28.7 | 26 | 28.4 | 30.7 |
| | Stability at 45° C. (days) | | | |
| | 0 | | 7 | |
| Liquid formulation | 30 | | 16 | |
| micropellets SG1 | 25.4 | | 25 | |
| micropellets SG2 | 28.7 | | 27.8 | |

These results show that the dried formulations SG1 and SG2 in the micro-pellet form are much more stable than the current liquid formulation. No significant antigenicity loss was measured after up to 3 months at 37° C. and 1 week at 45° C.

EXAMPLE 2

Manufacturing of Thermo-Stable Dry Vaccine Under Micropellet Form Containing Flu H5N1 (Indonesia) Antigens Adjuvanted with Aluminum Oxyhydroxide Gel This study compared the thermo-stability of the liquid H5N1 Indonesia flu vaccine to dry formulations of this same vaccine processed with the micropellet technology according to the present invention.

The vaccine contains 65.4 µg/ml of H5N1 Indonesia strain in the vaccinal buffer, adjuvanted by aluminum oxyhydroxide gel.

Formulated liquid product to be dried was obtained by mixing one volume of H5N1 vaccine with one volume of the stabilizing formulation SG1. (cf. Example 1 for SG1 composition)

FIG. 10 shows a flowchart of the formulation and drying procedure.

Formulated liquid product SG1 was prilled in order to generate calibrated droplets. Prilling parameters for this formulation and a 300 µm nozzle head were:

Product flow rate: 8 ml/min
nozzle frequency: 916 Hz

These droplets fell in a cryogenic chamber in which temperature was maintained below −110° C. by direct injection of liquid nitrogen or by flowing countercurrent very cold gas (t°<−110° C.). The droplets froze during their fall and formed calibrated frozen particles.

These frozen particles were then transferred on pre-cooled trays at −50° C. and loading on the pre-cooled shelves of the freeze-drier (−50° C.) in order to always keep the frozen pellets below their glass transition (which was evaluated between −30° C. and −40° C.) and to avoid any melting or aggregation of the particles. Once the freeze-drier was loaded, vacuum was pulled in the freeze-drying chamber to initiate conventional freeze-drying of the pellets as know by the state of the art. For these formulations, the following freeze-drying parameters were used: Primary drying: shelf temperature equal to −35° C., pressure equal to 50 µbars during 10 h. Secondary drying: shelf temperature equal to 20° C., pressure equal to 50 µbars during 3 h. Residual moisture of the micropellets was below 2%.

Micropellets samples were exposed 7 days at 37° C. and 45° C. Potency (µg of antigen/ml) was then measured for each sample by SRD method. Dry samples were rehydrated using water for injection prior to analysis. Dissolution was instantaneous. The table 6 summarizes the obtained results. Results are expressed in mean value µg/ml of antigen; N.D. stands for "Non Detectable Antigenicity".

TABLE 6

| SRD Titers µg/ml | Liquid formulation | Micropellet SG1 |
| --- | --- | --- |
| $T_0$ | 65.4 | 53.6 |
| 7 d@37° C. | 52.5 | 51.4 |

TABLE 6-continued

| SRD Titers µg/ml | Liquid formulation | Micropellet SG1 |
| --- | --- | --- |
| 7 d@45° C. | <7.0 | 47.9 |
| 7 d@55° C. | N.D. | 44.9 |

These results show that the dried formulation SG1 in the micro-pellet form is much more stable than the current liquid formulation. No significant antigenicity loss was measured after 1 week at 37° C. and at 45° C. A loss of approximately 15% was observed after 1 week at 55° C., which is close to the precision of the assay itself.

Figure 11:
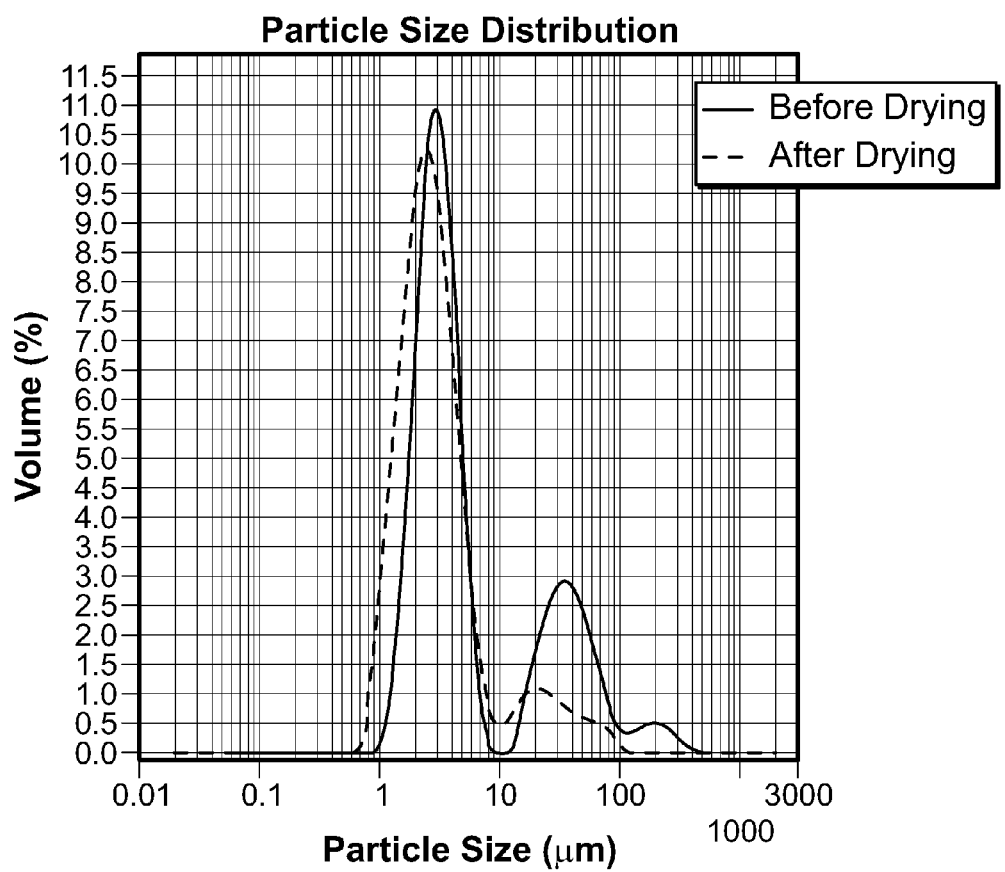

The impact of this drying process and the rehydration of the pellets on the adjuvant properties were evaluated by measuring the aluminum oxyhydroxide particle size distribution in the formulated bulk before drying, and after dissolution of the pellets using a particle size analyzer Malvern MasterSizer 2000. The results are given FIG. 11. We observed that this process did not induced aggregation of the gel.

Figure 12:
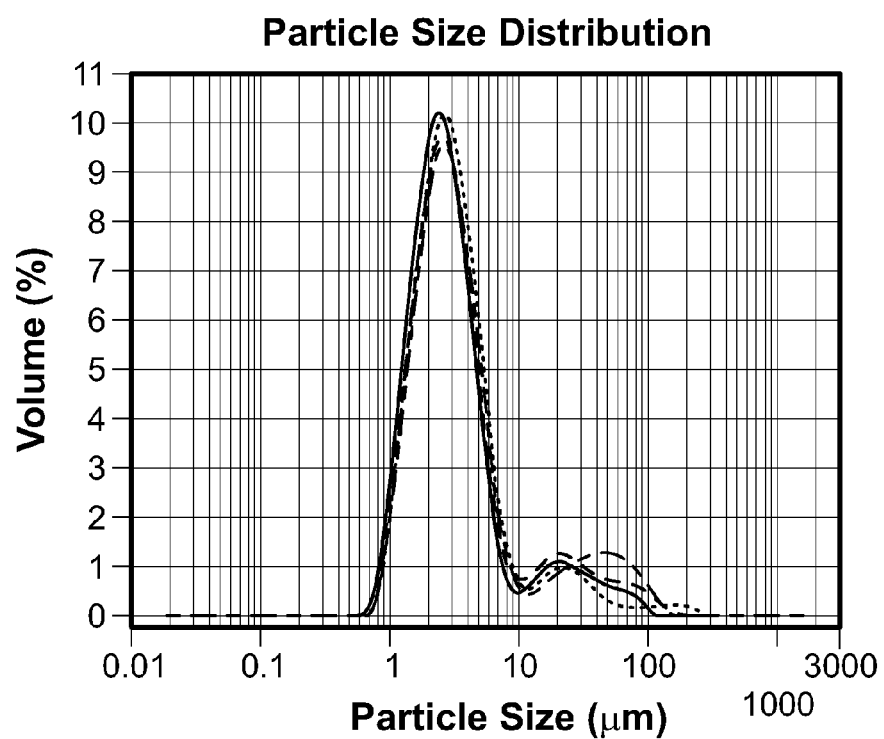

FIG. 12 also shows that the gel's size is maintained after thermostability incubation for at least 7 days at 37° C., 45° C. and 55° C., and demonstrates the stability of alum gel adjuvant in a micropellet form.

This example confirms the applicability of this technology to alum gel adjuvanted Flu antigens, and most generally, the feasibility to dry adjuvanted antigens with alum gels using the micropellet technology.

EXAMPLE 3

Manufacturing of Thermo-Stable Dry Vaccine Under Micropellet Form Containing Non-Adjuvanted Flu H5N1 (Indonesia) and Rehydration with an Adjuvant Emulsion This study compared the thermo-stability of the liquid H5N1 Indonesia flu vaccine to dry formulations of this same vaccine processed with the micropellet technology.

The vaccine contains 176 µg/ml of H5N1 Indonesia strain in the vaccinal buffer.

Formulated liquid product to be dried was obtained by mixing the H5N1 vaccine with the stabilizing formulation SG1, in order to target the desired antigen concentration and stabilizer contents. The formulation SG1 was evaluated (cf. Example 1 for SG1 composition)

FIG. 13 shows a flowchart of the formulation and drying procedure.

Formulated liquid product was prilled in order to generate calibrated droplets. Prilling parameters for this formulation and a 300 µm nozzle head were:

Product flow rate: 8 ml/min
nozzle frequency: 997 Hz

These droplets fell in a cryogenic chamber in which the temperature was maintained below −110° C. by direct injection of liquid nitrogen or by flowing countercurrent very cold gas (t°<−110° C.). The droplets froze during their fall and formed calibrated frozen particles.

These frozen particles were then transferred on pre-cooled trays at −50° C. and loading on the pre-cooled shelves of the freeze-drier (−50° C.) in order to always keep the frozen pellets below their glass transition (which was evaluated between −30° C. and −40° C.) and to avoid any melting or aggregation of the particles. Once the freeze-drier was loaded, vacuum was pulled in the freeze-drying chamber to initiate conventional freeze-drying of the pellets as know by the state of the art. For these formulations, the following freeze-drying parameters were used: Primary drying: shelf temperature equal to −35° C., pressure equal to 50 μbars during 10 h. Secondary drying: shelf temperature equal to 20° C., pressure equal to 50 μbars during 3 h. Residual moisture of the micropellets was below 2%.

In parallel, the same formulated product was generated, filled into vials and freeze-dried normally in a standard freeze-dryer. Filled vials were loaded on pre-cooled shelves at 5° C.; the product was then frozen down to −50° C. at 1° C./min and vacuum was pulled to initiate sublimation. Primary drying parameters were: shelf temperature equal to −18° C., pressure equal to 50 μbars during 16 h. Secondary drying parameters were: shelf temperature equal to 37° C., pressure equal to 50 μbars during 2 h.

Residual moisture of the freeze-dried product was also below 2%.

Micropellet and liquid samples were exposed to different time at 37° C., 45° C. and 55° C. Freeze-dried samples were exposed at 37° C. and 55° C. Potency (μg of antigen/ml) was then measured for each sample by SRD method. Dry samples were rehydrated using water for injection (WFI) prior to analysis. Dissolution was instantaneous. The tables 7, 8 and 9 summarize the obtained results respectively for a standard liquid formulation, dried micropellets and the freeze-dried product. Results are expressed in mean value μg/ml of antigen. Initial SRD Titer at To corresponds to the measured titer after reconstitution of the micropellets after processing.

TABLE 7

| Liquid H5N1 Stability study | Initial SRD Titer: $T_0$ = 14.1 μg/ml Time | | |
|---|---|---|---|
| SRD Titers μg/ml | 7 days | 1 month | 3 months |
| Thermostability at 37° C. | 11.6 | 5 | <5 |
| Thermostability at 45° C. | 3.4 | <5 | <5 |
| Thermostability at 55° C. | <5 | <5 | <5 |

TABLE 8

| Dry micropellets H5N1 Stability study SRD Titers μg/ml, | Initial SRD Titer: $T_0$ = 47.2 μg/ml Time | | |
|---|---|---|---|
| Rehydration WFI | 7 days | 1 month | 3 months |
| Thermostability at 37° C. | 53 | 47.3 | 50.1 |
| Thermostability at 45° C. | 51.6 | 47 | 41.1 |
| Thermostability at 55° C. | 49.5 | 45.4 | 47.3 |

TABLE 9

| Freeze-dried H5N1 Stability study SRD Titers μg/ml, | Initial SRD Titer: $T_0$ = 39.4 μg/ml Time | |
|---|---|---|
| Rehydration WFI | 14 days | 1 month |
| Thermostability at 37° C. | 36.9 | 38.1 |
| Thermostability at 55° C. | 35.6 | 35.1 |

These results show that the dried formulation SG1 in the micro-pellet form is much more stable than the current liquid formulation. No significant antigenicity loss was measured after 3 months at 37° C., 45° C. and 55° C. Results given table 9 confirm that standard freeze-drying also provides good thermostabilty.

Moreover, the data given table 10 show that no antigenicity loss was measured after 9 months at +5° C. These results are very promising for long term stability at +5° C. and room temperature over a several year time period.

The feasibility of rehydrating the H5N1 micropellets with an emulsion has been studied. The emulsion used for this study is the one described in the patent application WO 2007/006939. The same experimental plan as table 8 was performed but samples were rehydrated with the emulsion rather than water for injection. The results are given table 10 and table 11:

TABLE 10

| | H5N1 micropellet formulation (μg/ml) at To | H5N1 micropellet formulation (μg/ml) To +9 months at +5° C. |
|---|---|---|
| After Drying. Rehydration WFI | 47.2 | 54.8 |
| After Drying. Rehydration Emulsion | 49.2 | 51 |

TABLE 11

| Dry H5N1 Stability study SRD Titers μg/ml. | Initial SRD Titer: To = 49.2 μg/ml Time | | |
|---|---|---|---|
| Rehydration Emulsion | 7 days | 1 month | 3 months |
| Thermostability at 37° C. | 46.5 | 42.6 | 47.8 |
| Thermostability at 45° C. | 43.1 | 46.1 | 46.5 |
| Thermostability at 55° C. | 41.8 | 42.7 | 41.7 |

Table 10 proves that the dissolution of the micropellets with an emulsion as adjuvant does not impact the stability of the antigen and therefore its recovery. Table 11 confirms that this statement is also verified after thermostability incubation of the micropellets as all measured titers are comparable with titers measured after dissolution with water for injection.

Figure 14:
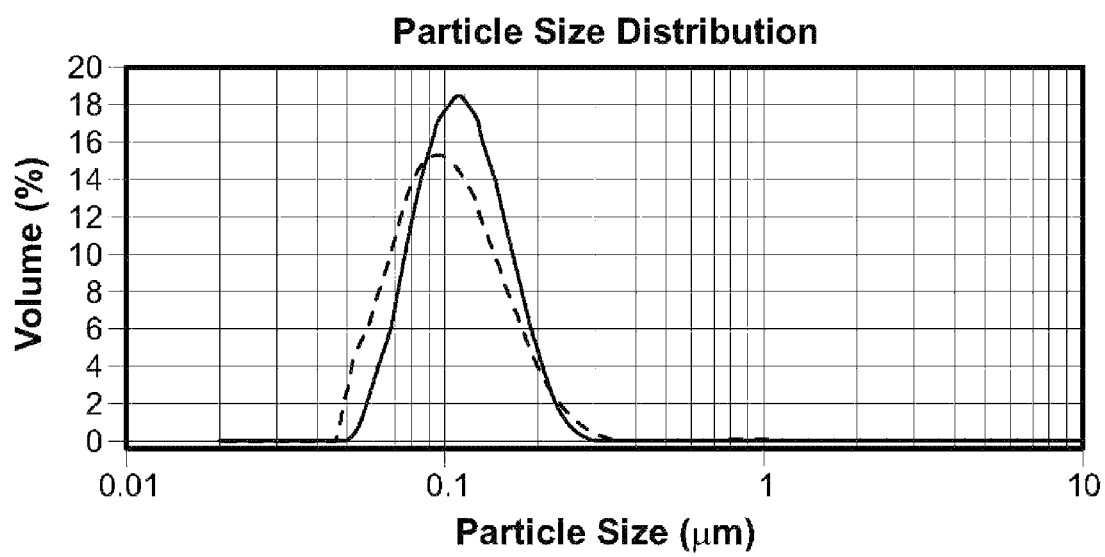
Figure 15:
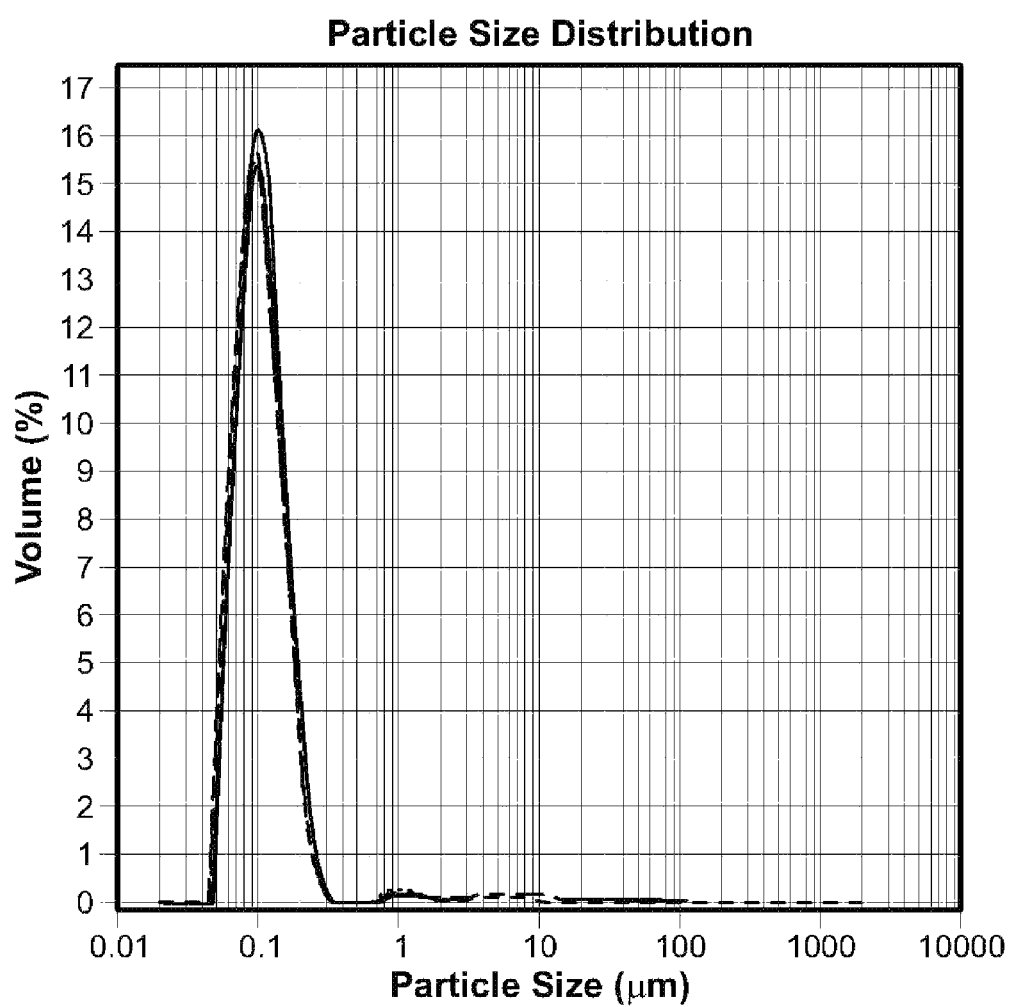

FIG. 14 shows a comparison of the size of the emulsion before rehydration of these micropellets and after dissolution. The superposition of the two size distributions confirms that the size of the emulsion, and therefore its integrity, is not significantly altered by the rehydration of a freeze-dried matrix. The size distribution remains monomodal and centered on 100 nm. Moreover, FIG. 15 confirms the stability of the size of the emulsion after dissolution of the micropellets and over a one hour storage period at room temperature.

This study confirms that, thanks to the micropellet technology, it is possible to use the adjuvant as a dissolution buffer and to avoid all interaction between the adjuvant and the antigen during the shelf life of the product.

EXAMPLE 4a

Manufacturing of a Thermo-Stable Dry Vaccine Under Micropellet Form Containing Non-Adjuvanted Flu H5N1 (Indonesia) with Different Sugars Used as Stabilizers This study shows the preparation of 3 stabilized dry influenza vaccine compositions each comprising a different disaccharide (trehalose, lactose and maltose respectively)

and the thermo-stability of such dry compositions processed with the micropellet technology.

The vaccine contains 131 μg/ml of H5N1 Indonesia strain in the vaccinal buffer.

The formulated liquid products to be dried were obtained by mixing the H5N1 vaccine with the stabilizing formulations SG5, SG6 and SG7, respectively (see tables 12a, 12b and 12c), in order to target the desired antigen concentrations and stabilizer contents.

TABLE 12a

SG5

| COMPONENTS | |
| --- | --- |
| quantity for | 1000 ml |
| Trehalose | 200 g |
| Adjustment pH @ 7.0 +/− 0.2 (NaOH, HCl) | |
| Water PPI | 1000 ml |

TABLE 12b

SG6

| COMPONENTS | |
| --- | --- |
| quantity for | 1000 ml |
| Lactose | 200 g |
| Adjustment pH @ 7.0 +/− 0.2 (NaOH, HCl) | |
| Water PPI | 1000 ml |

TABLE 12c

SG7

| COMPONENTS | |
| --- | --- |
| quantity for | 1000 ml |
| Maltose | 200 g |
| Adjustment pH @ 7.0 +/− 0.2 (NaOH, HCl) | |
| Water PPI | 1000 ml |

FIG. 13 shows a flowchart of the principle of the formulation and drying procedure with SG1 stabilizer as an example. Identical flowchart was used with SG5, SG6 and SG7 to obtain a disaccharide concentration of 15.4% (w/v) in the formulated product prior to prilling.

Each of the 3 formulated liquid products was prilled in order to generate calibrated droplets. Prilling parameters for these formulation and a 300 μm nozzle head were:

Product flow rate: 8 ml/min nozzle frequency: ranging from 994 Hz and 1001 Hz depending on the formulation These droplets fell in a cryogenic chamber in which the temperature was maintained below −110° C. by direct injection of liquid nitrogen or by flowing countercurrent very cold gas (t°<−110° C.). The droplets froze during their fall and formed calibrated frozen particles.

These frozen particles were then transferred on pre-cooled trays at −50° C. and loading on the pre-cooled shelves of the freeze-drier (−50° C.) in order to always keep the frozen pellets below their glass transition (which was evaluated between −30° C. and −40° C.) and to avoid any melting or aggregation of the particles. Once the freeze-drier was loaded, vacuum was pulled in the freeze-drying chamber to initiate conventional freeze-drying of the pellets as know by the state of the art. For these formulations, the following freeze-drying parameters were used: Primary drying: shelf temperature equal to −35° C., pressure equal to 50 μbars during 10 h. Secondary drying: shelf temperature equal to 20° C., pressure equal to 50 μbars during 3 h. Residual moisture of the micropellets was below 2%.

Micropellets samples were exposed to different time at 37° C. and 55° C. Potency (μg of antigen/ml) was then measured for each sample by SRD method. Dry samples were rehydrated using water for injection (WFI) prior to analysis. Dissolution was instantaneous. The tables 12d, 12e and 12f summarize the obtained thermostability results respectively for each of the 3 compositions in the form of dried micropellets. Results are expressed in mean value μg/ml of antigen. Initial SRD Titer at To corresponds to the measured titer after reconstitution of the micropellets after processing.

TABLE 12d

| Dry micropellets H5N1 + SG5 Stability study SRD Titers μg/ml, | Initial SRD Titer: To = 61.5 μg/ml Time | |
| --- | --- | --- |
| Rehydration WFI | 14 days | 1 month |
| Thermostability at 37° C. | 57.7 | 58.7 |
| Thermostability at 55° C. | 57.2 | 58.9 |

TABLE 12e

| Dry micropellets H5N1 + SG6 Stability study SRD Titers μg/ml, | Initial SRD Titer: To = 60.2 μg/ml Time | |
| --- | --- | --- |
| Rehydration WFI | 14 days | 1 month |
| Thermostability at 37° C. | 53.0 | 50.5 |
| Thermostability at 55° C. | 52.4 | 53.1 |

TABLE 12f

| Dry micropellets H5N1 + SG7 Stability study SRD Titers μg/ml, | Initial SRD Titer: To = 52.9 μg/ml Time | |
| --- | --- | --- |
| Rehydration WFI | 14 days | 1 month |
| Thermostability at 37° C. | 52.8 | 49.6 |
| Thermostability at 55° C. | 50.4 | 51.2 |

These results confirm a similar stability profile for a wide range of saccharide excipients used as stabilizer.

EXAMPLE 4b

Manufacturing of a Thermo-Stable Dry Vaccine Under Micropellet Form Containing Non-Adjuvanted Flu H5N1 (Indonesia) with 2% (w/v) Sucrose in the Formulated Bulk Ready to be Processed The vaccine contains 176 μg/ml of H5N1 Indonesia strain in the vaccinal buffer.

The formulated liquid product to be dried was obtained by mixing the H5N1 vaccine with the stabilizing formulation SG8, in order to target the desired antigen concentration and a stabilizer content of 2% (w/v). Table 12g shows the composition of the stabilizing formulation SG8.

TABLE 12g

| SG8 | |
| --- | --- |
| COMPONENTS | |
| quantity for | 1000 ml |
| Sucrose | 26 g |
| Adjustment pH @ 7.0 +/− 0.2 (NaOH, HCl) | |
| Water PPI | 1000 ml |

The micropellets made from the formulated liquid bulk containing 2% w/v sucrose (liquid bulk formulated with SG8) were obtained as described in example 4a. FIG. 16 shows a flowchart of the formulation and drying procedure.

The micropellet samples were exposed to different time at 37° C. and 55° C. Potency (μg of antigen/nil) was then measured for each sample by SRD method. Dry samples were rehydrated using water for injection (WFI) prior to analysis. Dissolution was instantaneous. Table 12 h shows the obtained results for the dried micropellets. The results are expressed in mean value μg/ml of antigen. Initial SRD Titer at To corresponds to the measured titer after reconstitution of the micropellets right after processing.

TABLE 12h

| Dry micropellets H5N1 + SG8 Stability study SRD Titers μg/ml, | Initial SRD Titer: To = 39.6 μg/ml Time | |
| --- | --- | --- |
| Rehydration WFI | 14 days | 1 month |
| Thermostability at 37° C. | 32.9 | 33.6 |
| Thermostability at 55° C. | 34.71 | 34.0 |

EXAMPLE 5

Study of the Impact of Micropellet Processing on Adjuvanted Diphtheria Toxoid (Dt) and Tetanus Toxoid (Tt) Vaccines The first part of this study evaluated the stability of TetanusTt and Dt antigens freeze-dried in a micropellet form either with or without pre-adsorption on aluminum gel ALOOH. Five formulations were prepared as described below.

Figure 17:
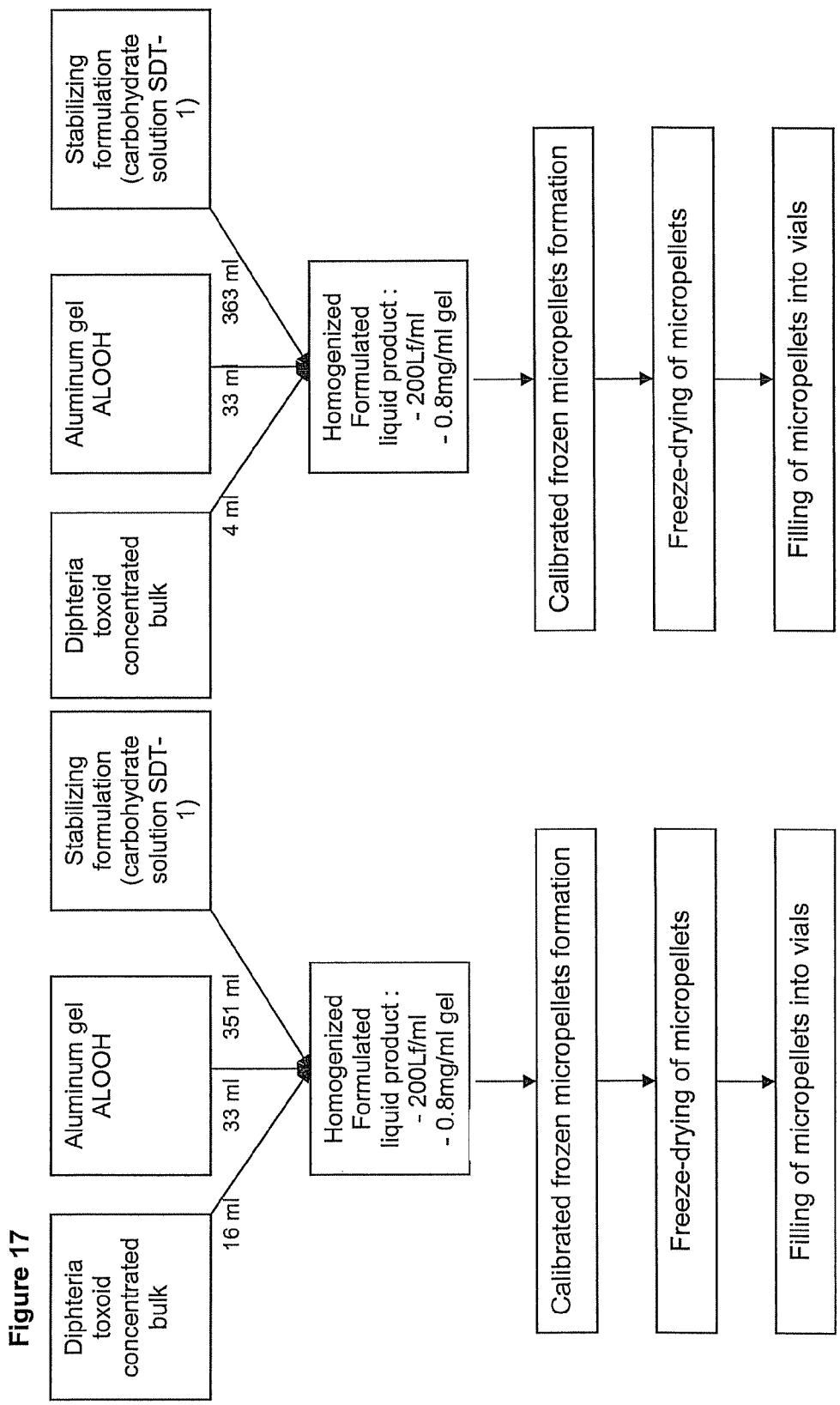

Formulated liquid products to be dried containing DiphtheriaDt or TetanusTt in presence of aluminum gel were obtained by mixing a given volume of *Diphtheria* or *Tetanus* toxoid concentrated bulk with aluminum gel and a stabilizer in order to obtain the following composition:

Dt (*Diphteria* toxoid) formulated product: 200 Lf/ml of antigen and 0.8 mg/ml of aluminum gel Tt (*Tetanus* toxoid) formulated product: 40 Lf/ml of antigen and 0.8 mg/ml of aluminum gel FIG. 17 shows a flowchart of the formulation and drying procedure of these two formulations Formulated liquid products to be dried containing DiphtheriaDt or TetanusTt without aluminum gel were obtained by mixing a given volume of *Diphtheria* or *Tetanus* toxoid concentrated bulk with a stabilizer in order to obtain the following composition:

Dt (*Diphtheria* toxoid) formulated product: 500 Lf/ml of antigen

Tt (*Tetanus* toxoid) formulated product: 100 Lf/ml of antigen

Figure 18:
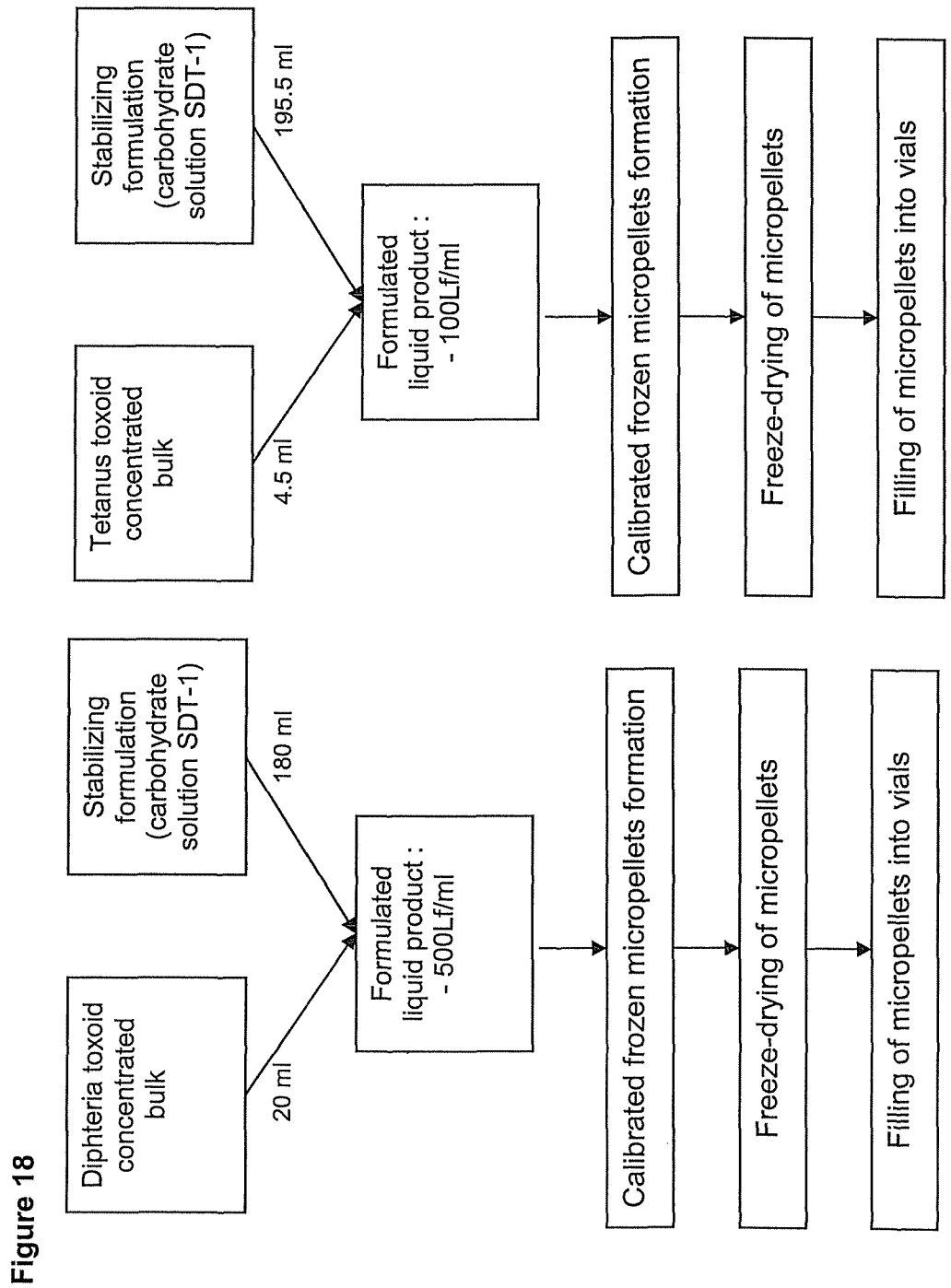

FIG. 18 shows a flowchart of the formulation and drying procedure of these two formulations.

Antigen contents for *Diphtheria* toxoid and *Tetanus* toxoid were measured using the rocket immuno-electrophoresis test, as performed by the state of the art.

Formulated liquid product to be dried containing only aluminum gel is obtained by mixing a given volume aluminum gel with a stabilizer in order to obtain the following composition:

Aluminum gel ALOOH formulated product: 2.4 mg/ml

Figure 19:
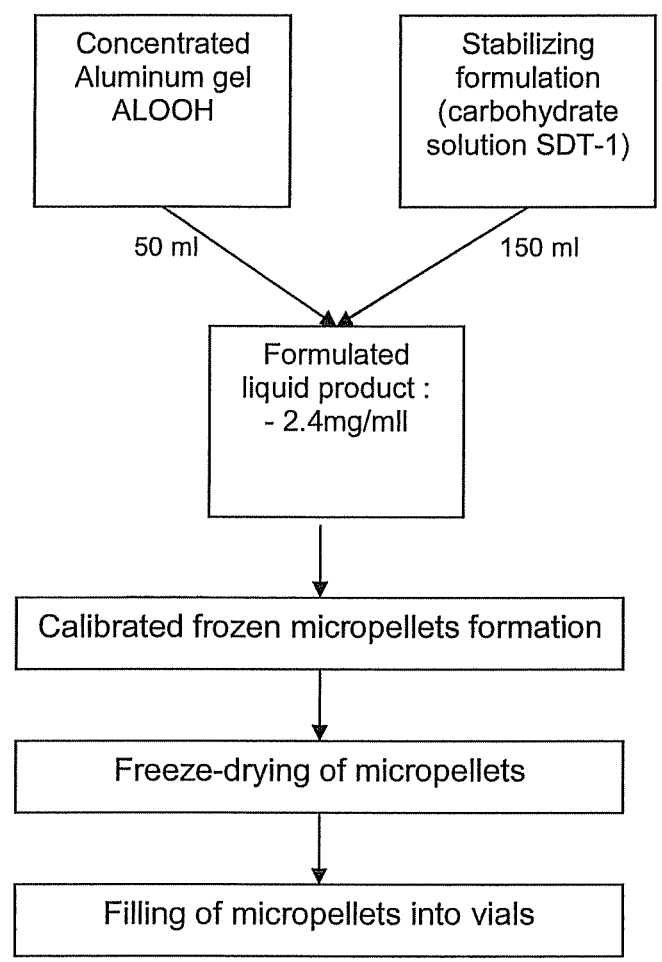

FIG. 19 shows a flowchart of the formulation and drying procedure of this formulation. The composition of the stabilizer used for this experiment, called SDT-1, is given in the table below:

TABLE 13

| SDT-1 | |
| --- | --- |
| Quantity for 1000 ml | |
| Sucrose | 100 g |
| Trehalose | 100 g |
| Tris 50 mM | 6.055 g |
| pH adjustment 7.0 +/− 0.2 (NaOH, HCl) | |
| Water for injection | 1000 mL |

Formulated liquid products were prilled in order to generate calibrated droplets. Prilling parameters for these formulations and a 300 μm nozzle head are summarized in the table below:

TABLE 14

| Flow rate | Diphtheria toxoid 8 ml/min | Tetanus toxoid 8 ml/min | Diphtheria toxoid + Al gel 8 ml/min | Tetanus toxoid + Al gel 8 ml/min | Al gel 8 ml/min |
| --- | --- | --- | --- | --- | --- |
| Frequency (Hz) | 1487 | 1543 | 1223 | 1282 | 1479 |

These droplets fell in a cryogenic chamber in which temperature was maintained below −110° C. by direct injection of liquid nitrogen or by flowing countercurrent very cold gas (t°<−110° C.). The droplets froze during their fall and formed calibrated frozen particles.

These frozen particles were then transferred on pre-cooled trays at −50° C. and loading on the pre-cooled shelves of the freeze-drier (−50° C.) in order to always keep the frozen pellets below their glass transition (which was evaluated between −30° C. and −40° C.) and to avoid any melting or aggregation of the particles. Once the freeze-drier was loaded, vacuum was pulled in the freeze-drying chamber to initiate conventional freeze-drying of the pellets as know by the state of the art. For these formulations, the following freeze-drying parameters were used: Primary drying: shelf temperature equal to −35° C., pressure equal to 50 μbars during 10 h. Secondary drying: shelf temperature equal to 20° C., pressure equal to 50 μbars during 3 h. Residual moisture of the micropellets was below 2%.

Micropellets samples were exposed at 37° C. and 55° C. Potency (Lf/ml) was measured for each sample by rocket immuno-electrophoresis test. Dry samples were re-hydrated using water for injection prior to analysis. Dissolution was instantaneous.

*Diphtheria* toxoid stability results:

TABLE 15

| Diphtheria Toxoid | Time (days) | | | |
|---|---|---|---|---|
| Target = 100 Lf/ml | 0 | 14 | 30 | 90 |
| Stability at 37° C. (Lf/ml) | 98.5 | 100.3 | 100 | 86.7 |
| Stability at 55° C. (Lf/ml) | 98.5 | 102.2 | 104 | 87.6 |

These results confirm no significant loss after up to 1 month at 37° C. and 55° C. and only about 13% loss after 3 months, which is at the limit of significance. Moreover, incubation of micropellets containing *Diphtheria* toxoid and alum gel showed that at all time points and all tested temperatures, 100% of the antigen remained adsorbed to the gel after dissolution. The observed stability of the gel size distribution after dissolution and thermo-stability study showed similar results as for flu H5N1 adjuvanted with alum gel (see example 2).

*Tetanus* toxoid stability results:

TABLE 16

| Tetanus Toxoid | Time (days) | | | |
|---|---|---|---|---|
| Target = 20 Lf/ml | 0 | 14 | 30 | 90 |
| Stability at 37° C. (Lf/ml) | 18.1 | 21.8 | 20.1 | 17.1 |
| Stability at 55° C. (Lf/ml) | 18.1 | 21.8 | 20.9 | 18 |

These results confirm no significant loss after up to 3 months at 37° C. and 55° C. Moreover, incubation of micropellets containing *Tetanus* toxoid and alum gel showed that at all time points and all tested temperatures, 100% of the antigen remained adsorbed to the gel after dissolution. The observed stability of the gel size distribution after dissolution and thermo-stability study showed similar results as for flu H5N1 adjuvanted with alum gel (see example 2).

These data confirm that the micropellet process allows obtaining thermostable dry adjuvanted or non-adjuvanted *Diphtheria* and *Tetanus* toxoid vaccines, when properly formulated, in terms of potency, adsorption state and adjuvant quality, up to 3 months at 55° C. without significant degradation. Moreover, aluminum gel could successfully be freeze-dried using the micropellet technology maintaining a comparable size distribution and avoiding massive aggregation.

EXAMPLE 6

Study of the Impact of Micropellet Processing on Aluminum Gel Characteristics: interactions with T (Tetanus Toxoid)

In this example, micropellets generated in example 5 were used. The goal of this study was to evaluate the impact of the micropellet processing on aluminum gel AlOOH adsorption capacity.

In 3 ml vials, a constant quantity of aluminum gel AlOOH of 0.3 mg, initially in a liquid or micropellet form, was mixed with different quantity of *Tetanus* toxoid (0.05, 0.1, 0.2, 0.3, 0.4, 0.5 et 0.75 mg total), initially in a liquid or micropellet form as well.

5 experiments were performed:
  Series 1: liquid mix of liquid aluminum gel AlOOH and bulk *Tetanus* toxoid antigen, in the absence of stabilizer
  Series 2: liquid mix of dissolved Aluminum gel AlOOH micropellets and bulk *Tetanus* toxoid antigen
  Series 3: liquid mix of liquid aluminum gel AlOOH, bulk *Tetanus* toxoid antigen and stabilizer
  Series 4: liquid mix of liquid aluminum gel AlOOH and dissolved *Tetanus* toxoid micropellets
  Series 5: Liquid mix of dissolved aluminum gel AlOOH micropellets and dissolved *Tetanus* toxoid micropellets Water and stabilizer contents were adjusted before dissolution of the micropellets in order to obtain a rehydrated solution strictly identical in all stabilizer containing formulations (Series 2 to 5).

After mixing the liquid products, the vials were incubated at room temperature in a wheel agitator during 2 hours and then centrifuged at 3000 rpm during 5 minutes. The non adsorbed *Tetanus* toxoid was quantified in the supernatant by Micro Bradford technique (Bio Rad protein assay). A *Tetanus* toxoid reference was tested for each series of samples in order to have a quantitative assay. The obtained results are summarized in the table below:

TABLE 17

| | Presence of stabilizer | Tetanus toxoid adsorption capacity mg toxoid/mg gel | Average mg toxoid/mg gel |
|---|---|---|---|
| Series 1 | No | 0.49<br>0.72 | 0.61 ± 0.12 |
| Series 2 | yes | 0.67 | 0.60 ± 0.07 |
| Series 3 | yes | 0.54<br>0.82<br>0.54 | 0.76 ± 0.22 |
| Series 4 | yes | 0.92<br>0.57<br>0.72 | 0.64 ± 0.08 |
| Series 5 | yes | 0.59<br>1.06<br>0.91 | 0.86 ± 0.26 |

These results confirm that the presence of a stabilizer does not have any significant negative impact on the adsorption capacity of the gel. Moreover, micropellet processing does not impact significantly, taking into account the variability of the method, adsorption capacity of alum gel when applied on *Tetanus* toxoid and/or alum gel.

The invention claimed is:

1. A stabilized dry *C. difficile* vaccine composition comprising micropellets or particles, wherein the micropellets or particles are prilled micropellets or particles with a diameter from about 200 μm to about 1500 μm, wherein the micropellets or particles are obtained by a process comprising, a) diluting a liquid bulk antigen composition comprising a protein antigen or an antigenic preparation from *C. difficile* with an aqueous solution comprising a carbohydrate, a sugar alcohol, or a mixture thereof in order to obtain a diluted vaccine composition solution wherein the concentration of the carbohydrate, sugar alcohol, or mixture thereof is from 2% (w/v) to the limit of solubility,
b) prilling the diluted vaccine composition solution to form calibrated droplets of the vaccine having a diameter of approximately from about 200 μm to about 1500 μm,
c) subjecting the droplets of the vaccine to freezing to form frozen spherical micropellets or particles of the vaccine, and
d) drying the frozen spherical micropellets or particles of the vaccine to form dry spherical micropellets or particles of the vaccine having a diameter from about 200 μm to about 1500 μm.

2. The composition as claimed in claim 1, wherein each micropellet or particle comprises one or more antigens from only one pathogen.

3. The composition as claimed in claim 1, wherein each micropellet or particle comprises one or more antigens from one or more different pathogens.

4. The composition as claimed in claim 1 further comprising an adjuvant.

5. The composition of claim 4, wherein the adjuvant is contained in separate dry spherical micropellets or particles.

6. A vaccine kit comprising a first container containing a composition according to claim 1 and a second container containing an aqueous solution for the reconstitution of the vaccine.

7. The kit as claimed in claim 6, wherein it comprises a third container containing a stabilized dry adjuvant composition in the form of dry spherical micropellets or particles.

8. The composition according to claim 1 further comprising prilled micropellets or particles comprising an antigen or antigens from a pathogen other than *C. difficile*.

9. A vaccine kit comprising a first container containing a composition according to claim 8 and a second container containing an aqueous solution for the reconstitution of the vaccine.

10. The kit as claimed in claim 9, wherein the aqueous solution comprises an adjuvant.

11. The kit as claimed in claim 9, wherein it comprises a third container containing a stabilized dry adjuvant composition in the form of dry spherical micropellets or particles.

\* \* \* \* \*